(12) United States Patent
Parker et al.

(10) Patent No.: US 12,329,527 B2
(45) Date of Patent: *Jun. 17, 2025

(54) METHOD AND DEVICE FOR DETECTING A NEURAL RESPONSE IN NEURAL MEASUREMENTS

(71) Applicant: Saluda Medical Pty Ltd, Artarmon (AU)

(72) Inventors: John Louis Parker, Artarmon (AU); Milan Obradovic, Artarmon (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 711 days.

This patent is subject to a terminal disclaimer.

(21) Appl. No.: 17/223,498

(22) Filed: Apr. 6, 2021

(65) Prior Publication Data

US 2021/0267518 A1    Sep. 2, 2021

Related U.S. Application Data

(63) Continuation of application No. 15/527,314, filed as application No. PCT/AU2015/050724 on Nov. 17, 2015, now Pat. No. 11,006,846.

(30) Foreign Application Priority Data

Nov. 17, 2014  (AU) ................................ 2014904595

(51) Int. Cl.
*A61B 5/24* (2021.01)
*A61B 5/00* (2006.01)
(Continued)

(52) U.S. Cl.
CPC ................ *A61B 5/24* (2021.01); *A61B 5/316* (2021.01); *A61B 5/388* (2021.01); *A61B 5/407* (2013.01);
(Continued)

(58) Field of Classification Search
CPC ....... A61B 5/0048; A61B 5/372; A61B 5/377; A61B 5/378; A61B 5/38; A61B 5/381;
(Continued)

(56) References Cited

U.S. PATENT DOCUMENTS 3,724,467 A    4/1973   Avery et al.
3,736,434 A    5/1973   Darrow
(Continued)

FOREIGN PATENT DOCUMENTS

AU    2013277009 B2    1/2016
CN       103648583 A    3/2014
(Continued)

OTHER PUBLICATIONS

Australian Examination Report for Application No. 2019283936, Mailed Apr. 1, 2021, 7 pages.
(Continued)

*Primary Examiner* — Puya Agahi
(74) *Attorney, Agent, or Firm* — Barnes & Thornburg LLP

(57) ABSTRACT

A method is provided for processing a neural measurement obtained in the presence of noise, in order to detect whether a locally evoked neural response is present in the neural measurement. A first neural measurement is obtained from a first sense electrode. A second neural measurement is contemporaneously obtained from a second sense electrode spaced apart from the first electrode along a neural pathway of the neural response. A neural response decay is determined, being a measure of the decay in the neural response from the first sense electrode to the second sense electrode. A ratio of the neural response decay to an amplitude normalising term is calculated. From the ratio it is determined whether a locally evoked neural response is present in the neural measurement.

23 Claims, 10 Drawing Sheets

(51) Int. Cl.
*A61B 5/316* (2021.01)
*A61B 5/388* (2021.01)
*A61B 5/389* (2021.01)
*A61N 1/36* (2006.01)
*G16H 40/63* (2018.01)

(52) U.S. Cl.
CPC .......... *A61B 5/7203* (2013.01); *A61B 5/7214* (2013.01); *A61B 5/7282* (2013.01); *G16H 40/63* (2018.01); *A61B 5/389* (2021.01); *A61B 5/4836* (2013.01); *A61N 1/36135* (2013.01)

(58) Field of Classification Search
CPC ..... A61B 5/383; A61B 5/4064; A61B 5/7203; A61B 5/7282
See application file for complete search history.

(56) References Cited

U.S. PATENT DOCUMENTS

| | | | |
|---|---|---|---|
| 3,817,254 A | 6/1974 | Maurer | |
| 3,898,472 A | 8/1975 | Long | |
| 4,158,196 A | 6/1979 | Crawford, Jr. | |
| 4,418,695 A | 12/1983 | Buffet | |
| 4,474,186 A | 10/1984 | Ledley et al. | |
| 4,628,934 A | 12/1986 | Pohndorf et al. | |
| 4,807,643 A | 2/1989 | Rosier | |
| 4,856,525 A | 8/1989 | van den Honert | |
| 5,113,859 A | 5/1992 | Funke | |
| 5,139,020 A | 8/1992 | Koestner et al. | |
| 5,143,081 A | 9/1992 | Young et al. | |
| 5,156,154 A | 10/1992 | Valenta, Jr. et al. | |
| 5,172,690 A | 12/1992 | Nappholz et al. | |
| 5,184,615 A | 2/1993 | Nappholz et al. | |
| 5,188,106 A | 2/1993 | Nappholz et al. | |
| 5,215,100 A | 6/1993 | Spitz et al. | |
| 5,324,311 A | 6/1994 | Acken | |
| 5,417,719 A | 5/1995 | Hull et al. | |
| 5,431,693 A | 7/1995 | Schroeppel | |
| 5,458,623 A | 10/1995 | Lu et al. | |
| 5,476,486 A | 12/1995 | Lu et al. | |
| 5,497,781 A | 3/1996 | Chen et al. | |
| 5,638,825 A | 6/1997 | Yamazaki et al. | |
| 5,702,429 A | 12/1997 | King et al. | |
| 5,758,651 A | 6/1998 | Nygard et al. | |
| 5,776,170 A | 7/1998 | Macdonald et al. | |
| 5,785,651 A | 7/1998 | Kuhn et al. | |
| 5,792,212 A | 8/1998 | Weijand et al. | |
| 5,814,092 A | 9/1998 | King | |
| 5,895,416 A | 4/1999 | Barreras et al. | |
| 5,913,882 A | 6/1999 | King | |
| 5,999,848 A | 12/1999 | Gord et al. | |
| 6,020,857 A | 2/2000 | Podger | |
| 6,027,456 A | 2/2000 | Feler et al. | |
| 6,038,480 A | 3/2000 | Hrdlicka et al. | |
| 6,066,163 A | 5/2000 | John | |
| 6,114,164 A | 9/2000 | Dennis et al. | |
| 6,144,881 A | 11/2000 | Hemming et al. | |
| 6,157,861 A | 12/2000 | Faltys et al. | |
| 6,212,431 B1 | 4/2001 | Hahn et al. | |
| 6,246,912 B1 | 6/2001 | Sluijter et al. | |
| 6,381,496 B1 | 4/2002 | Meadows et al. | |
| 6,449,512 B1 | 9/2002 | Boveja | |
| 6,463,328 B1 | 10/2002 | John | |
| 6,473,649 B1 | 10/2002 | Gryzwa et al. | |
| 6,473,653 B1 | 10/2002 | Schallhorn et al. | |
| 6,493,576 B1 | 12/2002 | Dankwart-Eder | |
| 6,516,227 B1 | 2/2003 | Meadows et al. | |
| 6,522,932 B1 | 2/2003 | Kuzma | |
| 6,600,955 B1 | 7/2003 | Zierhofer et al. | |
| 6,658,293 B2 | 12/2003 | Vonk et al. | |
| 6,675,046 B2 | 1/2004 | Holsheimer | |
| 6,782,292 B2 | 8/2004 | Whitehurst | |
| 6,895,280 B2 | 5/2005 | Meadows et al. | |
| 6,898,582 B2 | 5/2005 | Lange et al. | |
| 6,909,917 B2 | 6/2005 | Woods et al. | |
| 7,089,059 B1 | 8/2006 | Pless | |
| 7,171,261 B1 | 1/2007 | Litvak et al. | |
| 7,177,675 B2 | 2/2007 | Suffin et al. | |
| 7,206,640 B1 | 4/2007 | Overstreet | |
| 7,231,254 B2 | 6/2007 | DiLorenzo et al. | |
| 7,286,876 B2 | 10/2007 | Yonce et al. | |
| 7,412,287 B2 | 8/2008 | Yonce et al. | |
| 7,450,992 B1 | 11/2008 | Cameron | |
| 7,634,315 B2 | 12/2009 | Cholette | |
| 7,734,340 B2 | 6/2010 | De Ridder | |
| 7,742,810 B2 | 6/2010 | Moffitt | |
| 7,792,584 B2 | 9/2010 | Van Oort et al. | |
| 7,818,052 B2 | 10/2010 | Litvak et al. | |
| 7,831,305 B2 | 11/2010 | Gliner | |
| 7,835,804 B2 | 11/2010 | Fridman et al. | |
| 7,890,182 B2 | 2/2011 | Parramon et al. | |
| 7,894,905 B2 | 2/2011 | Pless et al. | |
| 8,083,685 B2 | 12/2011 | Fagin et al. | |
| 8,190,251 B2 | 5/2012 | Molnar et al. | |
| 8,224,459 B1 | 7/2012 | Pianca et al. | |
| 8,239,031 B2 | 8/2012 | Fried et al. | |
| 8,249,698 B2 | 8/2012 | Mugler et al. | |
| 8,332,047 B2 | 12/2012 | Libbus et al. | |
| 8,359,102 B2 | 1/2013 | Thacker et al. | |
| 8,401,655 B2 | 3/2013 | De Ridder | |
| 8,417,342 B1 | 4/2013 | Abell | |
| 8,454,529 B2 | 6/2013 | Daly et al. | |
| 8,494,645 B2 | 7/2013 | Spitzer et al. | |
| 8,515,545 B2 | 8/2013 | Trier | |
| 8,588,929 B2 | 11/2013 | Davis et al. | |
| 8,670,830 B2 | 3/2014 | Carlson et al. | |
| 8,886,323 B2 | 11/2014 | Wu et al. | |
| 9,044,155 B2 | 6/2015 | Strahl | |
| 9,155,892 B2 | 10/2015 | Parker et al. | |
| 9,302,112 B2 | 4/2016 | Bornzin et al. | |
| 9,381,356 B2 | 7/2016 | Parker et al. | |
| 9,386,934 B2 | 7/2016 | Parker et al. | |
| 9,872,990 B2 | 1/2018 | Parker et al. | |
| 9,974,455 B2 | 5/2018 | Parker et al. | |
| 10,206,596 B2 | 2/2019 | Single et al. | |
| 10,278,600 B2 | 5/2019 | Parker et al. | |
| 10,368,762 B2 | 8/2019 | Single | |
| 10,426,409 B2 | 10/2019 | Single | |
| 10,500,399 B2 | 12/2019 | Single | |
| 10,568,559 B2 | 2/2020 | Parker et al. | |
| 10,588,524 B2 | 3/2020 | Single et al. | |
| 10,588,698 B2 | 3/2020 | Parker et al. | |
| 10,632,307 B2 | 4/2020 | Parker | |
| 10,842,996 B2 | 11/2020 | Baru et al. | |
| 10,849,525 B2 | 12/2020 | Parker et al. | |
| 10,894,158 B2 | 1/2021 | Parker | |
| 10,918,872 B2 | 2/2021 | Parker et al. | |
| 11,006,846 B2 | 5/2021 | Parker et al. | |
| 11,006,857 B2 | 5/2021 | Parker | |
| 11,045,129 B2 | 6/2021 | Parker et al. | |
| 11,110,270 B2 | 9/2021 | Parker et al. | |
| 11,167,129 B2 | 11/2021 | Parker | |
| 11,172,864 B2 | 11/2021 | Parker et al. | |
| 11,179,091 B2 | 11/2021 | Karantonis et al. | |
| 11,191,966 B2 | 12/2021 | Wah | |
| 2002/0055688 A1 | 5/2002 | Katims | |
| 2002/0099419 A1 | 7/2002 | Ayal et al. | |
| 2002/0193670 A1 | 12/2002 | Garfield et al. | |
| 2003/0032889 A1 | 2/2003 | Wells | |
| 2003/0045909 A1 | 3/2003 | Gross et al. | |
| 2003/0139781 A1 | 7/2003 | Bradley et al. | |
| 2003/0153959 A1 | 8/2003 | Thacker et al. | |
| 2003/0195580 A1 | 10/2003 | Bradley et al. | |
| 2004/0088017 A1 | 5/2004 | Sharma et al. | |
| 2004/0116978 A1 | 6/2004 | Bradley | |
| 2004/0122482 A1 | 6/2004 | Tung et al. | |
| 2004/0158298 A1 | 8/2004 | Gliner | |
| 2004/0225211 A1 | 11/2004 | Gozani et al. | |
| 2004/0254494 A1 | 12/2004 | Spokoyny | |
| 2005/0010265 A1 | 1/2005 | Baru Fassio et al. | |
| 2005/0017190 A1 | 1/2005 | Eversmann et al. | |
| 2005/0021104 A1 | 1/2005 | DiLorenzo | |
| 2005/0065427 A1 | 3/2005 | Magill et al. | |

(56) References Cited

U.S. PATENT DOCUMENTS

| | | |
|---|---|---|
| 2005/0070982 A1 | 3/2005 | Heruth et al. |
| 2005/0075683 A1 | 4/2005 | Miesel et al. |
| 2005/0101878 A1 | 5/2005 | Daly et al. |
| 2005/0107674 A1 | 5/2005 | Parthasarathy et al. |
| 2005/0113877 A1 | 5/2005 | Giardiello et al. |
| 2005/0137670 A1 | 6/2005 | Christopherson et al. |
| 2005/0149154 A1 | 7/2005 | Cohen |
| 2005/0192567 A1 | 9/2005 | Katims |
| 2005/0203600 A1 | 9/2005 | Wallace |
| 2005/0209655 A1 | 9/2005 | Bradley et al. |
| 2005/0216064 A1 | 9/2005 | Heruth et al. |
| 2005/0282149 A1 | 12/2005 | Kovacs et al. |
| 2006/0009820 A1 | 1/2006 | Royle et al. |
| 2006/0020291 A1 | 1/2006 | Gozani et al. |
| 2006/0129205 A1 | 6/2006 | Boveja et al. |
| 2006/0135998 A1 | 6/2006 | Libbus et al. |
| 2006/0195159 A1 | 8/2006 | Bradley et al. |
| 2006/0212089 A1 | 9/2006 | Tass |
| 2006/0217782 A1 | 9/2006 | Boveja et al. |
| 2006/0264752 A1 | 11/2006 | Rubinsky et al. |
| 2006/0276722 A1 | 12/2006 | Litvak et al. |
| 2006/0287609 A1 | 12/2006 | Litvak et al. |
| 2007/0021800 A1 | 1/2007 | Bradley et al. |
| 2007/0073354 A1 | 3/2007 | Knudson et al. |
| 2007/0100378 A1 | 5/2007 | Maschino |
| 2007/0178579 A1 | 8/2007 | Ross et al. |
| 2007/0185409 A1 | 8/2007 | Wu et al. |
| 2007/0208394 A1 | 9/2007 | King et al. |
| 2007/0225765 A1 | 9/2007 | King |
| 2007/0225767 A1 | 9/2007 | Daly et al. |
| 2007/0244410 A1 | 10/2007 | Fridman et al. |
| 2007/0250120 A1 | 10/2007 | Flach et al. |
| 2007/0255372 A1 | 11/2007 | Metzler et al. |
| 2007/0265489 A1 | 11/2007 | Borgerding et al. |
| 2007/0282217 A1 | 12/2007 | McGinnis et al. |
| 2007/0287931 A1 | 12/2007 | Dilorenzo |
| 2008/0021292 A1 | 1/2008 | Stypulkowski |
| 2008/0051647 A1 | 2/2008 | Wu et al. |
| 2008/0064947 A1 | 3/2008 | Heruth et al. |
| 2008/0077191 A1 | 3/2008 | Morrell |
| 2008/0097529 A1 | 4/2008 | Parramon et al. |
| 2008/0132964 A1 | 6/2008 | Cohen et al. |
| 2008/0147155 A1 | 6/2008 | Swoyer |
| 2008/0183076 A1 | 7/2008 | Witte et al. |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1 | 12/2008 | Cholette |
| 2008/0319508 A1 | 12/2008 | Botros et al. |
| 2009/0030337 A1 | 1/2009 | Gozani et al. |
| 2009/0033486 A1 | 2/2009 | Costantino et al. |
| 2009/0058635 A1 | 3/2009 | Lalonde et al. |
| 2009/0082691 A1 | 3/2009 | Denison et al. |
| 2009/0149912 A1 | 6/2009 | Dacey, Jr. et al. |
| 2009/0157155 A1 | 6/2009 | Bradley |
| 2009/0270957 A1 | 10/2009 | Pianca |
| 2009/0281594 A1 | 11/2009 | Wacnik et al. |
| 2009/0287277 A1 | 11/2009 | Conn et al. |
| 2009/0299214 A1 | 12/2009 | Wu et al. |
| 2009/0306491 A1 | 12/2009 | Haggers |
| 2009/0306533 A1 | 12/2009 | Rousche et al. |
| 2010/0010388 A1 | 1/2010 | Panken et al. |
| 2010/0057159 A1 | 3/2010 | Lozano |
| 2010/0058126 A1 | 3/2010 | Chang et al. |
| 2010/0069835 A1 | 3/2010 | Parker |
| 2010/0069996 A1 | 3/2010 | Strahl |
| 2010/0070007 A1 | 3/2010 | Parker |
| 2010/0070008 A1 | 3/2010 | Parker |
| 2010/0100153 A1 | 4/2010 | Carlson et al. |
| 2010/0106231 A1 | 4/2010 | Torgerson |
| 2010/0114237 A1 | 5/2010 | Giftakis et al. |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs, II |
| 2010/0179626 A1 | 7/2010 | Pilarski |
| 2010/0191307 A1 | 7/2010 | Fang et al. |
| 2010/0204748 A1 | 8/2010 | Lozano et al. |
| 2010/0222844 A1 | 9/2010 | Troosters et al. |
| 2010/0222858 A1 | 9/2010 | Meloy |
| 2010/0249643 A1 | 9/2010 | Gozani et al. |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1 | 2/2011 | Chian |
| 2011/0040546 A1 | 2/2011 | Gerber et al. |
| 2011/0077712 A1 | 3/2011 | Killian |
| 2011/0087085 A1 | 4/2011 | Tsampazis et al. |
| 2011/0093042 A1 | 4/2011 | Torgerson et al. |
| 2011/0106100 A1 | 5/2011 | Bischoff |
| 2011/0130802 A1 | 6/2011 | Libbus et al. |
| 2011/0184488 A1 | 7/2011 | De Ridder et al. |
| 2011/0204811 A1 | 8/2011 | Pollmann-retsch |
| 2011/0224665 A1 | 9/2011 | Crosby et al. |
| 2011/0224749 A1 | 9/2011 | Ben-David et al. |
| 2011/0264165 A1 | 10/2011 | Molnar et al. |
| 2011/0270343 A1 | 11/2011 | Buschman et al. |
| 2011/0288391 A1 | 11/2011 | Rao et al. |
| 2011/0307030 A1 | 12/2011 | John |
| 2011/0313310 A1 | 12/2011 | Tomita |
| 2011/0313483 A1 | 12/2011 | Hincapie et al. |
| 2012/0029377 A1 | 2/2012 | Polak |
| 2012/0059275 A1 | 3/2012 | Fagin et al. |
| 2012/0101552 A1 | 4/2012 | Lazarewicz et al. |
| 2012/0101826 A1 | 4/2012 | Visser et al. |
| 2012/0109004 A1 | 5/2012 | Cadwell |
| 2012/0109236 A1 | 5/2012 | Jacobson et al. |
| 2012/0155183 A1 | 6/2012 | Aritome |
| 2012/0185020 A1 | 7/2012 | Simon et al. |
| 2012/0245481 A1 | 9/2012 | Blanco et al. |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2012/0310301 A1 | 12/2012 | Bennett et al. |
| 2013/0041449 A1 | 2/2013 | Cela et al. |
| 2013/0053722 A1 | 2/2013 | Carlson et al. |
| 2013/0060302 A1 | 3/2013 | Polefko et al. |
| 2013/0172774 A1 | 7/2013 | Crowder et al. |
| 2013/0289661 A1 | 10/2013 | Griffith et al. |
| 2013/0289683 A1 | 10/2013 | Parker et al. |
| 2014/0046407 A1 | 2/2014 | Ben-ezra et al. |
| 2014/0066803 A1 | 3/2014 | Choi |
| 2014/0142447 A1 | 5/2014 | Takahashi et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0243931 A1 | 8/2014 | Parker et al. |
| 2014/0249396 A1 | 9/2014 | Shacham-diamand et al. |
| 2014/0276195 A1 | 9/2014 | Papay et al. |
| 2014/0277250 A1 | 9/2014 | Su et al. |
| 2014/0277267 A1 | 9/2014 | Vansickle et al. |
| 2014/0288551 A1 | 9/2014 | Bharmi et al. |
| 2014/0288577 A1 | 9/2014 | Robinson et al. |
| 2014/0296737 A1 | 10/2014 | Parker et al. |
| 2014/0324118 A1 | 10/2014 | Simon et al. |
| 2014/0350634 A1 | 11/2014 | Grill et al. |
| 2014/0358024 A1 | 12/2014 | Nelson et al. |
| 2015/0018699 A1 | 1/2015 | Zeng et al. |
| 2015/0025597 A1 | 1/2015 | Surth et al. |
| 2015/0032181 A1 | 1/2015 | Baynham et al. |
| 2015/0051637 A1 | 2/2015 | Osorio |
| 2015/0126839 A1 | 5/2015 | Li et al. |
| 2015/0148869 A1 | 5/2015 | Dorvall, II et al. |

(56) References Cited

U.S. PATENT DOCUMENTS

| | | |
|---|---|---|
| 2015/0164354 A1 | 6/2015 | Parker et al. |
| 2015/0174396 A1 | 6/2015 | Fisher et al. |
| 2015/0238104 A1 | 8/2015 | Tass |
| 2015/0238304 A1 | 8/2015 | Lamraoui |
| 2015/0282725 A1 | 10/2015 | Single |
| 2015/0313487 A1 | 11/2015 | Single |
| 2015/0360031 A1 | 12/2015 | Bornzin et al. |
| 2015/0374999 A1 | 12/2015 | Parker |
| 2016/0082265 A1 | 3/2016 | Moffitt et al. |
| 2016/0082268 A1 | 3/2016 | Hershey et al. |
| 2016/0101289 A1 | 4/2016 | Stolen et al. |
| 2016/0106980 A1 | 4/2016 | Sürth et al. |
| 2016/0121124 A1 | 5/2016 | Johanek et al. |
| 2016/0129272 A1 | 5/2016 | Hou et al. |
| 2016/0144189 A1 | 5/2016 | Bakker et al. |
| 2016/0166164 A1 | 6/2016 | Obradovic et al. |
| 2016/0175594 A1 | 6/2016 | Min et al. |
| 2016/0287126 A1 | 10/2016 | Parker et al. |
| 2016/0287182 A1 | 10/2016 | Single |
| 2016/0367808 A9 | 12/2016 | Simon et al. |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0157410 A1 | 6/2017 | Moffitt et al. |
| 2017/0173326 A1 | 6/2017 | Bloch et al. |
| 2017/0173335 A1 | 6/2017 | Min et al. |
| 2017/0173341 A1 | 6/2017 | Johanek et al. |
| 2017/0216587 A1 | 8/2017 | Parker |
| 2017/0361101 A1 | 12/2017 | Single |
| 2018/0071513 A1 | 3/2018 | Weiss et al. |
| 2018/0104493 A1 | 4/2018 | Doan et al. |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |
| 2018/0228391 A1 | 8/2018 | Parker et al. |
| 2018/0228547 A1 | 8/2018 | Parker |
| 2018/0229046 A1 | 8/2018 | Parker et al. |
| 2018/0256052 A1 | 9/2018 | Parker et al. |
| 2019/0001139 A1 | 1/2019 | Mishra et al. |
| 2019/0030339 A1 | 1/2019 | Baru et al. |
| 2019/0125269 A1 | 5/2019 | Markovic et al. |
| 2019/0168000 A1 | 6/2019 | Laird-wah |
| 2019/0216343 A1 | 7/2019 | Single et al. |
| 2019/0239768 A1 | 8/2019 | Karantonis et al. |
| 2019/0307341 A1 | 10/2019 | Parker et al. |
| 2019/0357788 A1 | 11/2019 | Single |
| 2020/0029914 A1 | 1/2020 | Single |
| 2020/0129108 A1 | 4/2020 | Parker et al. |
| 2020/0155240 A1 | 5/2020 | Parker et al. |
| 2020/0215331 A1 | 7/2020 | Single |
| 2020/0282208 A1 | 9/2020 | Parker |
| 2021/0001133 A1 | 1/2021 | Williams et al. |
| 2021/0008373 A1 | 1/2021 | Single et al. |
| 2021/0016091 A1 | 1/2021 | Parker et al. |
| 2021/0121696 A1 | 4/2021 | Parker et al. |
| 2021/0308449 A1 | 10/2021 | Parker |
| 2021/0315502 A1 | 10/2021 | Parker et al. |
| 2021/0379386 A1 | 12/2021 | Parker et al. |
| 2021/0387005 A1 | 12/2021 | Parker et al. |
| 2021/0387008 A1 | 12/2021 | Single |
| 2021/0393964 A1 | 12/2021 | Single et al. |
| 2022/0007987 A1 | 1/2022 | Huang et al. |
| 2022/0039724 A1 | 2/2022 | Parker et al. |
| 2022/0151535 A1 | 5/2022 | Parker et al. |
| 2022/0151536 A1 | 5/2022 | Karantonis et al. |
| 2022/0168574 A1 | 6/2022 | Wah |
| 2022/0249009 A1 | 8/2022 | Parker et al. |
| 2022/0287620 A1 | 9/2022 | Parker |

FOREIGN PATENT DOCUMENTS

| | | |
|---|---|---|
| CN | 103654762 A | 3/2014 |
| CN | 103842022 A | 6/2014 |
| CN | 104411360 A | 3/2015 |
| EP | 0219084 A2 | 4/1987 |
| EP | 1244496 A1 | 10/2002 |
| EP | 0998958 B1 | 8/2005 |
| EP | 2019716 A | 11/2007 |
| EP | 2243510 A2 | 10/2010 |
| EP | 2443995 A2 | 4/2012 |
| EP | 2520327 A2 | 11/2012 |
| EP | 2707095 A1 | 3/2014 |
| EP | 3229893 A1 | 10/2017 |
| JP | 2006504494 A | 2/2006 |
| JP | 2009512505 A | 3/2009 |
| JP | 2012524629 | 10/2012 |
| JP | 2013500779 A | 1/2013 |
| JP | 2013527784 A | 7/2013 |
| JP | 2013536044 A | 9/2013 |
| JP | 2014522261 A | 9/2014 |
| JP | 2014523261 A | 9/2014 |
| WO | 1983003191 A | 9/1983 |
| WO | 1993001863 A1 | 2/1993 |
| WO | 1996012383 A1 | 4/1996 |
| WO | 2000002623 A1 | 1/2000 |
| WO | 2002036003 A1 | 11/2001 |
| WO | 2002038031 | 5/2002 |
| WO | 2002049500 A2 | 6/2002 |
| WO | 2002082982 A1 | 10/2002 |
| WO | 2003028521 A2 | 4/2003 |
| WO | 2003043690 | 5/2003 |
| WO | 2003103484 A2 | 12/2003 |
| WO | 2004021885 A1 | 3/2004 |
| WO | 2004103455 | 12/2004 |
| WO | 2005032656 A1 | 4/2005 |
| WO | 2005105202 A1 | 11/2005 |
| WO | 2005122887 A2 | 12/2005 |
| WO | 2006091636 A2 | 8/2006 |
| WO | 2007050657 A1 | 5/2007 |
| WO | 2007064936 A1 | 6/2007 |
| WO | 2007127926 A2 | 11/2007 |
| WO | 2007130170 A1 | 11/2007 |
| WO | 2008004204 A1 | 1/2008 |
| WO | 2008049199 A1 | 5/2008 |
| WO | 2009002072 A2 | 12/2008 |
| WO | 2009002579 A1 | 12/2008 |
| WO | 2009010870 A2 | 1/2009 |
| WO | 2009130515 A2 | 10/2009 |
| WO | 2009146427 A1 | 12/2009 |
| WO | 2010013170 A1 | 2/2010 |
| WO | 2010044989 A2 | 4/2010 |
| WO | 2010051392 A1 | 5/2010 |
| WO | 2010051406 A1 | 5/2010 |
| WO | 2010057046 A2 | 5/2010 |
| WO | 2010124139 A1 | 10/2010 |
| WO | 2010138915 A1 | 12/2010 |
| WO | 2011011327 A1 | 1/2011 |
| WO | 2011014570 A1 | 2/2011 |
| WO | 2011017778 A1 | 2/2011 |
| WO | 2011066477 A1 | 6/2011 |
| WO | 2011066478 A1 | 6/2011 |
| WO | 2011112843 A1 | 9/2011 |
| WO | 2011119251 A2 | 9/2011 |
| WO | 2011159545 A2 | 12/2011 |
| WO | 2012016138 A1 | 2/2012 |
| WO | 2012027252 A2 | 3/2012 |
| WO | 2012027791 A1 | 3/2012 |
| WO | 2012155183 A1 | 11/2012 |
| WO | 2012155184 A1 | 11/2012 |
| WO | 2012155185 A1 | 11/2012 |
| WO | 2012155187 A1 | 11/2012 |
| WO | 2012155188 A1 | 11/2012 |
| WO | 2012155189 A1 | 11/2012 |
| WO | 2012155190 A1 | 11/2012 |
| WO | 2012162349 A1 | 11/2012 |
| WO | 2013063111 A1 | 5/2013 |
| WO | 2013075171 A1 | 5/2013 |
| WO | 2013116161 A1 | 8/2013 |

(56) References Cited

FOREIGN PATENT DOCUMENTS

| WO | 2014071445 | A1 | 5/2014 |
|---|---|---|---|
| WO | 2014071446 | A1 | 5/2014 |
| WO | 2014143577 | A1 | 9/2014 |
| WO | 2014150001 | A1 | 9/2014 |
| WO | 2015070281 | A1 | 5/2015 |
| WO | 2015074121 | A1 | 5/2015 |
| WO | 2015109239 | A1 | 7/2015 |
| WO | 2015143509 | A1 | 10/2015 |
| WO | 2015168735 | A1 | 11/2015 |
| WO | 2016011512 | A1 | 1/2016 |
| WO | 2016048974 | A1 | 3/2016 |
| WO | 2016059556 | A1 | 4/2016 |
| WO | 2016077882 | A1 | 5/2016 |
| WO | 2016090420 | A1 | 6/2016 |
| WO | 2016090436 | A1 | 6/2016 |
| WO | 2016115596 | A1 | 7/2016 |
| WO | 2016161484 | A2 | 10/2016 |
| WO | 2016168798 | A1 | 10/2016 |
| WO | 2016191807 | A1 | 12/2016 |
| WO | 2016191808 | A1 | 12/2016 |
| WO | 2016191815 | A1 | 12/2016 |
| WO | 2017053504 | A1 | 3/2017 |
| WO | 2017142948 | A1 | 8/2017 |
| WO | 2017173493 | A1 | 10/2017 |
| WO | 2017210352 | A1 | 12/2017 |
| WO | 2017219096 | A1 | 12/2017 |
| WO | 2018080753 | A1 | 5/2018 |
| WO | 2018119220 | A1 | 6/2018 |
| WO | 2018160992 | A1 | 9/2018 |
| WO | 2018170141 | A1 | 9/2018 |
| WO | 2019178634 | A1 | 9/2019 |
| WO | 2019204884 | A1 | 10/2019 |
| WO | 2019231796 | A1 | 12/2019 |
| WO | 2020082118 | A1 | 4/2020 |
| WO | 2020082126 | A1 | 4/2020 |
| WO | 2020082128 | A1 | 4/2020 |
| WO | 2020087123 | A1 | 5/2020 |
| WO | 2020087135 | A1 | 5/2020 |
| WO | 2020124135 | A1 | 6/2020 |
| WO | 2021007615 | A1 | 1/2021 |

OTHER PUBLICATIONS

European Search Report for European Application 12785619.3 Search Completed Oct. 13, 2014, Mailed Oct. 23, 2014, 7 pgs.
European Search Report for European Application 12785669.8 Search Completed Sep. 22, 2014, Mailed Sep. 29, 2014, 5 pgs.
European Search Report for European Application No. 15861444.6, Search completed Jul. 13, 2018, Mailed Jul. 23, 2018, 8 pgs.
Extended European Search Report for EP Application 12785483.4 completed Sep. 16, 2014, 7 pgs.
Extended European Search Report for European Application No. 11820923.8, report completed Dec. 9, 2013, report mailed Dec. 17, 2013, 6 pgs.
Extended European Search Report for European Application No. 13852669.4, Search completed Jun. 8, 2016, Mailed Jun. 22, 2016, 09 Pgs.
Extended European Search Report for European Application No. 14861553.7, Search completed Jun. 8, 2017, Mailed Jun. 19, 2017, 8 Pgs.
Extended European Search Report for European Application No. 14863597.2, Search completed Jun. 6, 2017, Mailed Jun. 13, 2017, 9 Pgs.
Extended European Search Report for European Application No. 15768956.3, Search completed Oct. 3, 2017, Mailed Oct. 10, 2017, 8 Pgs.
Extended European Search Report for European Application No. 15789515.2, Search completed Dec. 4, 2017, Mailed Jan. 30, 2018, 7 Pgs.
Extended European Search Report for European Application No. 16739680.3, Search completed Jun. 1, 2018, Mailed Jun. 12, 2018, 9 Pgs.
Extended European Search Report for European Application No. 16802237.4, Search completed Dec. 11, 2018, Mailed Dec. 19, 2018, 9 Pgs.
Extended European Search Report for European Application No. 16802238.2, Search completed Oct. 17, 2018, Mailed Oct. 24, 2018, 8 Pgs.
Extended European Search Report for European Application No. 17778477.4, report completed Nov. 12, 2019, mailed Nov. 20, 2019, 7 pgs.
Extended European Search Report for European Application No. 17814341.8, report completed Dec. 12, 2019, report mailed Jan. 2, 2020, 8 pgs.
Extended European Search Report for European Application No. 13853514.1, Search completed Jun. 8, 2016, Mailed Jun. 15, 2016, 07 Pgs.
International Preliminary Report for International Application No. PCT/AU2017/050296, Issued Oct. 9, 2018, 7 Pgs.
International Preliminary Report for International Application No. PCT/AU2017/050647, Issued Dec. 25, 2018, 8 pgs.
International Preliminary Report on Patentability for International Application No. PCT/AU2011/001127, Report Issued Mar. 5, 2013, 9 pgs.
International Preliminary Report on Patentability for International Application No. PCT/AU2012/000511, Report Issued Nov. 19, 2013, 6 pgs.
International Preliminary Report on Patentability for International Application No. PCT/AU2012/000512, Report Issued Nov. 19, 2013, 8 pgs.
International Preliminary Report on Patentability for International Application No. PCT/AU2012/000513, Report Issued Nov. 19, 2013, 11 pgs.
International Preliminary Report on Patentability for International Application No. PCT/AU2012/000515, Report Issued Nov. 19, 2013, 5 pgs.
International Preliminary Report on Patentability for International Application No. PCT/AU2012/000516, Report Issued Nov. 19, 2013, 9 pgs.
International Preliminary Report on Patentability for International Application No. PCT/AU2012/000517, Report Issued Nov. 19, 2013, 6 pgs.
International Preliminary Report on Patentability for International Application No. PCT/AU2012/000518, Report Issued Nov. 19, 2013, 11 pgs.
International Preliminary Report on Patentability for International Application No. PCT/AU2012/001441, Report Issued May 27, 2014, 10 pgs.
International Preliminary Report on Patentability for International Application No. PCT/AU2013/001279, Report Issued May 12, 2015, 6 pgs.
International Preliminary Report on Patentability for International Application No. PCT/AU2013/001280, Report Issued May 12, 2015, 6 pgs.
International Preliminary Report on Patentability for International Application No. PCT/AU2014/001049, Report Issued May 17, 2016, 5 pgs.
International Preliminary Report on Patentability for International Application No. PCT/AU2014/050369, Report Issued May 24, 2016, 8 pgs.
International Preliminary Report on Patentability for International Application No. PCT/AU2015/050135, Report Issued Oct. 4, 2016, 13 pgs.
International Preliminary Report on Patentability for International Application No. PCT/AU2015/050215, Report Issued Nov. 8, 2016, 4 pgs.
International Preliminary Report on Patentability for International Application No. PCT/AU2015/050422, Report Issued Jan. 31, 2017, 8 pgs.
International Preliminary Report on Patentability for International Application No. PCT/AU2015/050724, Report Issued May 23, 2017, 5 pgs.
International Preliminary Report on Patentability for International Application No. PCT/AU2015/050753, Report Issued Jun. 13, 2017, 7 pgs.

(56) References Cited

OTHER PUBLICATIONS

International Preliminary Report on Patentability for International Application No. PCT/AU2015/050787, Report Issued Jun. 13, 2017, 6 pgs.
International Preliminary Report on Patentability for International Application No. PCT/AU2016/050019, Report Issued Jul. 25, 2017, 9 pgs.
International Preliminary Report on Patentability for International Application No. PCT/AU2016/050263, Report Issued Oct. 10, 2017, 9 pgs.
International Preliminary Report on Patentability for International Application No. PCT/AU2018/050278, Issued Sep. 29, 2020, 7 pgs.
International Preliminary Report on Patentability for International Application No. PCT/AU2019/050384, Mailed Oct. 27, 2020, 8 pgs.
International Search Report & Written Opinion for International Application No. PCT/AU2013/001280, Search Completed Jan. 16, 2014, Mailed Jan. 16, 2014, 8 Pgs.
International Search Report & Written Opinion for International Application PCT/AU2013/001279, Search Completed Jan. 9, 2014, Mailed Jan. 9, 2014, 9 Pgs.
International Search Report and Written Opinion for International Application No. PCT/AU2011/001127, date completed Nov. 11, 2011, date mailed Nov. 15, 2011, 13 pgs.
International Search Report and Written Opinion for International Application No. PCT/AU2012/001441, International Filing Date Nov. 23, 2012, Search Completed Feb. 26, 2013, Mailed Feb. 26, 2013, 14 pgs.
International Search Report and Written Opinion for International Application No. PCT/AU2014/001049, Search completed Feb. 10, 2015, Mailed Feb. 10, 2015, 8 Pgs.
International Search Report and Written Opinion for International Application No. PCT/AU2014/050369, Search completed Feb. 20, 2015, Mailed Feb. 20, 2015, 14 Pgs.
International Search Report and Written Opinion for International Application No. PCT/AU2015/050135, Search completed Jun. 30, 2015, Mailed Jun. 30, 2015, 26 Pgs.
International Search Report and Written Opinion for International Application No. PCT/AU2015/050422, Search completed Oct. 14, 2015, Mailed Oct. 14, 2015, 17 Pgs.
International Search Report and Written Opinion for International Application No. PCT/AU2015/050724, Search completed May 9, 2016, Mailed May 9, 2016, 8 Pgs.
International Search Report and Written Opinion for International Application No. PCT/AU2015/050753, Search completed Feb. 10, 2016, Mailed Feb. 10, 2016, 10 Pgs.
International Search Report and Written Opinion for International Application No. PCT/AU2015/050787, Search completed Mar. 16, 2016, Mailed Mar. 16, 2016, 10 Pgs.
International Search Report and Written Opinion for International Application No. PCT/AU2016/050019, Search completed May 4, 2016, Mailed May 4, 2016, 16 Pgs.
International Search Report and Written Opinion for International Application No. PCT/AU2016/050263, Search completed Nov. 16, 2016, Mailed Nov. 16, 2016, 8 Pgs.
International Search Report and Written Opinion for International Application No. PCT/AU2016/050430, Search completed Aug. 16, 2016, Mailed Aug. 16, 2016, 10 Pgs.
International Search Report and Written Opinion for International Application No. PCT/AU2016/050431, Search completed Aug. 16, 2016, Mailed Aug. 16, 2016, 11 Pgs.
International Search Report and Written Opinion for International Application No. PCT/AU2016/050439, Search completed Jul. 15, 2016, Mailed Jul. 15, 2016, 8 Pgs.
International Search Report and Written Opinion for International Application No. PCT/AU2017/050296, Search completed Jul. 28, 2017, Mailed Jul. 28, 2017, 10 Pgs.
International Search Report and Written Opinion for International Application No. PCT/AU2017/050647, Search completed Sep. 29, 2017, Mailed Sep. 29, 2017, 13 Pgs.
International Search Report and Written Opinion for International Application No. PCT/AU2018/050278, Search completed Jun. 18, 2018, Mailed Jun. 18, 2018, 12 Pgs.
International Search Report and Written Opinion for International Application No. PCT/AU2019/050384, Search completed Jun. 25, 2019, Mailed Jun. 25, 2019, 15 Pgs.
International Search Report and Written Opinion for International Application No. PCT/AU2015/050215, Search completed Jul. 30, 2015, Mailed Jul. 30, 2015, 8 Pgs.
International Search Report for Australian Application 2011901829 Search Completed Feb. 6, 2012, Mailed Feb. 7, 2012, 3 pgs.
International Search Report for International Application No. PCT/AU2012/000511, International Filing Date May 11, 2012, Search Completed May 17, 2012, Mailed May 18, 2012, 4 pgs.
International Search Report for International Application No. PCT/AU2012/000512, International Filing Date May 11, 2012, Search Completed Jul. 10, 2012, Mailed Jul. 11, 2012, 4 pgs.
International Search Report for International Application No. PCT/AU2012/000513, International Filing Date May 11, 2012, Search Completed May 29, 2012, Mailed May 30, 2012, 5 pgs.
International Search Report for International Application No. PCT/AU2012/000515, International Filing Date May 11, 2012, Search Completed May 21, 2012, Mailed Jun. 4, 2012, 5 pgs.
International Search Report for International Application No. PCT/AU2012/000516, International Filing Date May 11, 2012, Search Completed Jul. 11, 2012, Mailed Jul. 12, 2012, 8 pgs.
International Search Report for International Application No. PCT/AU2012/000517, International Filing Date May 11, 2012, Search Completed Jun. 4, 2012, Mailed Jun. 6, 2012, 3 pgs.
International Search Report for International Application No. PCT/AU2012/000518, International Filing Date May 11, 2012, Search Completed Jun. 8, 2012, Mailed Jun. 12, 2012, 4 pgs.
International Search Report for International Application No. PCT/AU2019/051151, International Filing Date Oct. 22, 2019, Search Completed Feb. 24, 2020, Mailed Feb. 24, 2020, 9 pgs.
International Search Report for International Application No. PCT/AU2019/051160, International Filing Date Oct. 23, 2019, Search Completed Jan. 28, 2020, Mailed Jan. 28, 2020, 13 pgs.
International Search Report for International Application No. PCT/AU2019/051163, International Filing Date Oct. 23, 2019, Search Completed Jan. 21, 2020, Mailed Jan. 31, 2020, 8 pgs.
International Search Report for International Application No. PCT/AU2019/051197, International Filing Date Oct. 30, 2019, Search Completed Jan. 21, 2020, Mailed Jan. 21, 2020, 15 pgs.
International Search Report for International Application No. PCT/AU2019/051210, International Filing Date Nov. 2, 2019, Search Completed Feb. 4, 2020, Mailed Feb. 4, 2020, 10 pgs.
International Type Search Report for International Application No. AU 2015902393, Search completed May 16, 2016, Mailed May 16, 2016, 8 Pgs.
Japanese Office Action for Application No. 2017-546830, Mailed Feb. 20, 2020, 5 pages with English translation.
Japanese Office Action for Application No. 2017-553090, Mailed Mar. 16, 2020, 12 pages with English translation.
Japanese Office Action for Application No. 2018-552138, Mailed Mar. 1, 2021, 7 pages with English translation.
Japanese Office Action for Application No. 2018-513699, Mailed Jun. 8, 2020, 7 pages with English translation.
Massachusetts Institute of Technology, The Compound Action Potential of the Frog Sciatic Nerve, Quantitative Physiology: Cells and Tissues. Fall, 1999, Retrieved from http://umech.mit.edu/freeman/6.021J/2001/lab.pdf on May 22, 2012.
Medtronic, Spinal Cord Stimulation, RestoreSensor Neurostimulator, Features and Specification: Specification, Printed Jun. 16, 2014, 2 pgs.
Medtronic, Spinal Cord Stimulation, RestoreSensor Neurostimulator, Features and Specification: Summary Printed Jun. 16, 2014, 1 pg.
Office Action for Chinese Patent Application No. 201680020725.4, dated Mar. 16, 2020, 8 pgs.
Partial European Search Report for European Application No. 16775966.1, Search completed Oct. 26, 2018, Mailed Nov. 6, 2018, 11 Pgs.

(56) References Cited

OTHER PUBLICATIONS

Written Opinion for International Application No. PCT/AU2012/000511, International Filing Date May 11, 2012, Search Completed May 17, 2012, Mailed May 18, 2012, 5 pgs.
Written Opinion for International Application No. PCT/AU2012/000512, International Filing Date May 11, 2012, Search Completed Jul. 10, 2012, Mailed Jul. 11, 2012, 7 pgs.
Written Opinion for International Application No. PCT/AU2012/000513, International Filing Date May 11, 2012, Search Completed May 29, 2012, Mailed May 30, 2012, 10 pgs.
Written Opinion for International Application No. PCT/AU2012/000515, International Filing Date May 11, 2012, Search Completed May 21, 2012, Mailed Jun. 4, 2012, 4 pgs.
Written Opinion for International Application No. PCT/AU2012/000516, International Filing Date May 11, 2012, Search Completed Jul. 11, 2012, Mailed Jul. 12, 2012, 8 pgs.
Written Opinion for International Application No. PCT/AU2012/000517, International Filing Date May 11, 2012, Search Completed Jun. 4, 2012, Mailed Jun. 6, 2012, 5 pgs.
Written Opinion for International Application No. PCT/AU2012/000518, International Filing Date May 11, 2012, Search Completed Jun. 8, 2012, Mailed Jun. 12, 2012, 10 pgs.
Medtronic, RestoreSensor Neurostimulator, Retrieved from: http://web.archive.org/web/20150328092923/http://professional.medtronic.com:80/pt/neuro/scs/prod/restore-sensor/features-specifications/index.htm,, Capture Date Jul. 9, 2012, Printed on May 11, 2017.
"Advanced Pain Therapy using Neurostimulation for Chronic Pain", Medtronic RestoreSensor clinical trial paper, Clinical summary, 2011-11, pp. 32.
"Battelle Neurotechnology—Moving Beyond The Limits In Neurotechnology", Battelle, www.battelle.org, May 2014, pp. 1-2.
"Evoke 12C Percutaneous Leads", Saluda Medical, specifications available in the "Evoke Surgical Guide", version 6, http://www.saludamedical.com/manuals/, retrieved May 2017.
"Haptic technology", Wikipedia, Retrieved from: http://en.wikipedia.org/wiki/Haptic_technology, Last modified on Sep. 15, 2014, Printed on Sep. 15, 2014, 5 pgs.
"Implants for surgery, Cardiac pacemakers", IS-1 standard ISO 5841-3-2000, Oct. 15, 2000.
"Neural Bypass Technology Enables Movement in Paralyzed Patient", Posted on Jul. 29, 2014, 6 a.m. in Brain chips/computer interface, pp. 1-2.
"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.
"Wide bandwidth BioAmplifier", http://www.psylab.com/html/default_bioamp.htm, Printed Jan. 30, 2014, 1-3 pages.
Alam et al., "Evaluation of optimal electrode configurations for epidural spinal cord stimulation in cervical spinal cord injured rats", Journal of Neuroscience Methods, Mar. 2015, 28 pgs.
Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.
Andreassen et al., "Muscle Fibre Conduction Velocity in Motor Units of the Human Anterior Tibial Muscle: a New Size Principle Parameter", J. Physiol, (1987), 391, pp. 561-571.
Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.
Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.
Bahmer et al., "Effects of electrical pulse polarity shape on intra cochlear neural responses in humans: Triphasic pulses with cathodic second phase", Hearing Research, 2013, vol. 306, pp. 123-130.
Baltuch et al., "Deep brain stimulation for Parkinson's disease", CRC Press, 2007, 108.
Balzer et al., "Localization of cervical and cervicomedullary stimulation leads for pain treatment using median nerve somatosensay evoked potential collision testing", Journal of Neurosurgery, Jan. 2011, vol. 114, No. 1: pp. 200-205.
Blum, A. R. "An Electronic System for Extracellular Neural Stimulation and Recording", Dissertation, Georgia Institute of Technology, Aug. 2007, Retrieved from http://smartech.gatech.edu/handle/1853/16192 on Jan. 30, 2012.
Borg et al., "Conduction velocity and refractory period of single motor nerve fibres in antecedent poliomyelitis", Journal of Neurology, Neurosurgery, and Psychiatry, vol. 50, 1987, pp. 443-446.
Bratta et al., "Orderly Stimulation of Skeletal Muscle Motor Units with Tripolar Nerve Cuff Electrode", IEEE Transactions on Biomedical Engineering, vol. 36, No. 8, 1989.
Brown et al., "Impact of Deep Brain Stimulation on Upper Limb Askinesia in Parkinson's Disease", Annals of Neurology, 45, No. 4, 1999, pp. 473-488.
Budagavi et al., "Modelling of compound nerve action potentials health and disease", Engineering in Medicine and Biology Society, 1992 14th Annual International Conference of the IEEE. vol. 6. IEEE, 1992. pp. 2600-2601.
Celestin et al., "Pretreatment Psychosocial Variables as Predictors of Outcomes Following Lumbar Surgery and Spinal Cord Stimulation: A Systematic Review and Literature Synthesis", American Academy of Pain Medicine, 2009, vol. 10, No. 4, pp. 639-653. doi: 10.1111/j.1526-4637.2009.00632.X.
Cong et al., "A 32-channel modular bi-directional neural interface system with embedded DSP for closed-loop operation", 40th European Solid State Circuits Conference (ESSCIRC), 2014, pp. 99-102.
Connolly et al., "Towards a platform for prototyping control systems for optimization of neuromodulation therapies", IEEE Biomedical Circuits and Systems Conference (BioCAS), 2015, pp. 1-4.
Coquery et al., "Backward and forward masking in the perception of cutaneous stimuli", Perception & Psychophysics, 1973, vol. 13.No. 2, pp. 161-163.
Dawson, G. D., "The relative excitability and conduction velocity of sensory and motor nerve fibres in man", Journal of Physiology, 1956, vol. 131(2), pp. 436-451.
De Ridder et al., "Burst Spinal Cord Stimulation toward Paresthesia-Free Pain Suppression", Nuerosurgery-online.com, May 2010, vol. 66, No. 8, pp. 986-990.
Delgado et al., "Measurement and interpretation of electrokinetic phenomena", Pure Appl. Chem., 2005, vol. 77, No. 10, pp. 1753-1805.
Devergnas et al., A "Cortical potentials evoked by deep brain stimulation in the subthalamic area", Frontiers in System Neuroscience, May 13, 2011, vol. 5, Article 30, 2011, doi: 10.3389/fnsys.2011.00030.
Dijkstra, E. A. "Ultrasonic Distance Detection for a Closed-Loop Spinal Cord Stimulation System", Proceedings—19th International Conference—IEEE/EMBS Oct. 30-Nov. 2, 1997, Chicago, IL., 4 pgs.
Dillier, N et al., "Measurement of the electrically evoked compound action potential via a neural response telemetry system", Ann. Otol. Rhinol. Laryngol., vol. 111, No. 5, May 2002, pp. 407-414.
Doiron et al., "Persistent Na+ Current Modifies Burst Discharge By Regulating Conditional Backpropagation of Dendritic Spikes", Journal of Neurophysiology 89, No. 1 (Jan. 1, 2003): 324-337, doi:10.1152/jn.00729.2002.
England et al., "Increased Numbers of Sodium Channels Form Along Demyelinated Axons", Brain Research 548, No. 1-2 (May 10, 1991): pp. 334-337.
Fagius, J. et al. "Sympathetic Reflex Latencies and Conduction Velocities in Normal Man", Journal of Neurological Sciences, 1980. vol. 47, pp. 433-448.
Falowski et al., "Spinal Cord Stimulation: an update", Neurotherapeutics: The Journal of the American Society for Experimental NeuroTherapeutics 5, No. 1, Jan. 2008, pp. 86-99.
Fisher, "F-Waves—Physiology and Clinical Uses", TheScientificWorldJournal, (2007) 7, pp. 144-160.
Fitzpatrick et al., "A Nerve Cuff Design for the Selective Activation and Blocking of Myelinated Nerve Fibers", IEEE Engineering in Medicine and Biology Society, vol. 13, No. 2, 1991.

(56) References Cited

OTHER PUBLICATIONS

Franke et al., Felix "An Online Spike Detection and Spike Classification Algorithm Capable of Instantaneous Resolution of Overlapping Spikes", Journal of Computational Neuroscience, 2010, vol. 29, No. 1-2, pp. 127-148.
French et al., "Information transmission at 500 bits/s by action potentials in a mechanosensory neuron of the cockroach", Neuroscience Letters, vol. 243, No. 1-3, Feb. 1, 1998, pp. 113-116.
Fuentes et al., "Spinal Cord Stimulation Restores Locomotion in Animal Models of Parkinson's Disease", Science, vol. 323, No. 5921, Mar. 20, 2009, pp. 1578-1582.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs., http://www.jneuroengrehab.com/content/10/1/2.
George et al., "Vagus nerve stimulation: a new tool for brain research and therapy", Biological Psychiatry 47, No. 4, Feb. 15, 2000, pp. 287-295.
Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003.816077.
Goodall et al., "Modeling Study of Activation and Propagation delays During Stimulation of Peripheral Nerve Fibres with a Tripolar Cuff Electrode", IEEE Transactions on Rehabilitation Engineering, Sep. 1995, vol. 3, No. 3, pp. 272-282.
Gorman et al., "ECAP Mapping of the Spinal Cord: Influence of Electrode Position on Aβ Recruitment", (2012)., In 16th Annual Meeting. Presented at the North American Neuromodulation Society, Las Vegas, NV, 2 pgs.
Gorman et al., "Neural Recordings For Feedback Control Of Spinal Cord Stimulation: Reduction Of Paresthesia Variability.", 2013, In International Neuromodulation Society 11th World Congress, presented at the International Neuromodulation Society 11th World Congress, Berlin, Germany, 2 pgs.
Hallstrom et al, "Distribution of lumbar spinal evoked potentials and their correlation with stimulation-induced paresthesiae", Electroencephalography and Clinical Neurophysiology, Mar.-Apr. 1991, vol. 80, No. 2, pp. 126-139, doi:10.1016/0168-5597(91)90150-V.
Harper et al., "Conduction Velocity is Related to Morphological Cell Type in Rat Dorsal Root Ganglion Neurones", J. Physiol, (1985), vol. 359, pp. 31-46.
He et al., "Perception threshold and electrode position for spinal cord stimulation", Pain, vol. 59, (1994), pp. 55-63.
Herreras, "Local Field Potentials: Myths and Misunderstandings", Frontiers in Neural Circuits, Dec. 15, 2016, vol. 10, Article 1101, 16 pgs., doi:10.3389/fncir.2016.00101.
Holsheimer et al., "Optimum Electrode Geometry for Spinal Cord Stimulation: the Narrow Bipole and Tripole", Medical and Biological Engineering and Computing, 1997, vol. 35, No. 5, pp. 493-497.
Holsheimer et al., "Significance of the Spinal Cord Position in Spinal Cord Stimulation", Acta Neurochir (1995) [Suppl] 64, pp. 119-124.
Holsheimer et al., "Spinal Geometry and Paresthesia Coverage in Spinal Cord Stimulation", Neuromodulation, 1998, vol. 1, No. 3, pp. 129-136.
Howell et al., "Evaluation of Intradural Stimulation Efficiency and Selectivity in a Computational Model of Spinal Cord Stimulation", Plos One, DOI:10.1371/journal.pone.0114938, Dec. 23, 2014.
Huff, Terry B. et al., "Real-Time CARS Imaging Reveals a Calpain-Dependent Pathway for Paranodal Myelin Retraction during High-Frequency Stimulation", PLoS One, vol. 6, Issue 3 (Mar. 3, 2011): e17176, 11 pgs., doi:10.1371/journal.pone.0017176.
Jeffrey et al., "A reliable method for intracranial electrode implantation and chronic electrical stimulation in the mouse brain", BMC Neuroscience. Biomed Central. London, GB. vol. 14. No. 1, Aug. 6, 2013 (Aug. 6, 2013), pp. 1-8.

Jones et al., "Scaling of Electrode-Electrolyte Interface Model Parameters In Phosphate Buffered Saline", IEEE Transactions on Biomedical Circuits and Systems, 2015, vol. 9, No. 3, pp. 441-448.
Kent, "Characterization of Evoked Potentials During Deep Brain Stimulation in the Thalamus", Dissertation, Duke University. Retrieved from https://hdl.handle.net/10161/8195, 2013, https://dukespace.lib.duke.edu/dspace/handle/10161/8195.
Kent et al., "Instrumentation to Record Evoked Potentials for Closed-Loop Control of Deep Brain Stimulation", Conf. Proc. IEEE Eng. Med Biol. Sol, Aug. 2012, pp. 6777-6780, doi:10.1109/IEMBS.20113.6091671.
Kent et al., AR "Recording evoked potentials during deep brain stimulation: development and validation of instrumentation to suppress the stimulus artefact", J Neural Eng., Jun. 2012, vol. 9, No. 3, 036004, doi: 10.1088/1741-2560/9/3/036004.
Kim et al., "A Wavelet-Based Method for Action Potential Detection From Extracellular Neural Signal Recording With Low Signal-to-Noise Ratio", IEEE Transactions On Biomedical Engineering, Aug. 2003, vol. 50. No. 8, pp. 999-1011.
Kim et al., "Cell Type-specific Changes of the Membrane Properties of Peripherally-axotomized Dorsal Root Ganglion Neurons in a Rat Model of Neuropathic Pain", Neuroscience, vol. 86, No. 1, May 21, 1998, pp. 301-309, doi:10.1016/S0306-4522(98)00022-0.
Kopelman et al., "Attempted Reversible Sympathetic Ganglion Block by An Implantable Neurostimulator", Interactive CardioVascular and Thoracic Surgery, Feb. 7, 2012, vol. 14, Issue 5, pp. 605-609, doi:10.1093/icvts/ivr137.
Krames et al., "Neuromodulation", 1st Edition, Academic Press, 2009, pp. 540-541.
Krarup, Christian "Compound sensory action potential in normal and pathological human nerves", Muscle & Nerve, Apr. 2004, vol. 29, No. 4, pp. 465-483.
Krishnan et al., "Excitability Differences in Lower-Limb Motor Axons During and After Ischemia", Muscle & nerve, vol. 31, No. 2 (2005), pp. 205-213.
Kumar et al., "Deep Brain Stimulation for Intractable Pain: a 15-year Experience", Neurosurgery, Issue 40, No. 4, Apr. 1997, pp. 736-747.
Kumar et al., "Double-blind evaluation of subthalamic nucleus deep brain stimulation in advanced Parkinson's disease", by the American Academy of Neurology, 51, No. 3, Sep. 1, 1998, pp. 850-855.
Kumar et al., "Globus Pallidus Deep Brain Stimulation for Generalized Dystonia: Clinical and PET Investigation", Sep. 11, 1999, vol. 53, No. 4, pp. 871-874, doi:10.1212/WNL.53.4.871.
Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.
Lempka, Scott "The Electrode-Tissue Interface During Recording and Stimulation In The Central Nervous System", Thesis, 155 pgs., published May 2010.
Levy et al., "Incidence and Avoidance of Neurologic Complications with Paddle Type Spinal Cord Stimulation Leads", Neuromodulation, Sep. 2011, vol. 14, No. 15, pp. 412-422, https://doi.org/10.1111/j.1525-1403.2011.00395.x.
Li, S. et al., "Resonant antidromic cortical circuit activation as a consequence of high-frequency subthalamic deep-brain stimulation", J Neurophysiol. Dec. 2007; 98(6): 3525-37. First published Oct. 10, 2007. doi:10.1152/jn.00808.2007.
Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/jn.00855.2002.
Macefield, "Spontaneous and Evoked Ectopic Discharges Recorded from Single Human Axons", Muscle & Nerve 21, No. 4, Apr. 1998, pp. 461-468.
Mahnam et al., "Measurement of the current-distance relationship using a novel refractory interaction technique", J. Neural Eng. 6(2): 036005, published May 20, 2009, 22 pgs.
Markandey, Vishal "ECG Implementation on the TMS320C5515 DSP Medical Development Kit (MDK)", Texas Instruments Application Report Jun. 2010, 35 pgs.

(56) References Cited

OTHER PUBLICATIONS

Matzner et al., "Na+ Conductance and the Threshold for Repetitive Neuronal Firing", Brain Research 597, No. 1 (Nov. 27, 1992): 92-98, doi: 10.1016/0006-8993(92)91509-D.
McGill, Kevin et al., "On the Nature and Elimination of Stimulus Artifact in Nerve Signals Evoked and Recorded Using Surface Electrodes", IEEE Transactions On Biomedical Engineering, vol. BME-29, No. 2, Feb. 1982, pp. 129-137.
Melzack et al., "Pain mechanisms: a new theory", Science, New York, New York, vol. 150, No. 3699, Nov. 19, 1965, pp. 971-979.
Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-445.
Misawa et al., "Neuropathic Pain Is Associated with Increased Nodal Persistent Na(+) Currents in Human Diabetic Neuropathy", Journal of the Peripheral Nervous System: JPNS, 14, No. 4 (Dec. 2009): 279-284.
Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi: 10.1016/0304-3959(84)90013-7.
North et al., "Prognostic value of psychological testing in patients undergoing spinal cord stimulation: a prospective study", Neurosurgery, Aug. 1, 1996, vol. 39, Issue 2, pp. 301-311. https://doi.org/10.1097/00006123-199608000-00013.
Oakley et al., "Spinal Cord Stimulation: Mechanisms of Action", Spine 27, No. 22, Nov. 15, 2002, pp. 2574-2583.
Oakley et al., "Transverse Tripolar Spinal Cord Stimulation: Results of an International Multicenter Study", Neuromodulation, vol. 9, No. 3, 2006, pp. 192-203.
Obradovic et al., "Effect of pressure on the spinal cord during spinal cord stimulation in an animal model", Poster, 18th Annual Meeting of the North American Neuromodulation Society, Dec. 11-14, 2014, Las Vegas.
Oh et al., "Long-term hardware-related complications of deep brain stimulation", Neurosurgery, vol. 50, No. 6, Jun. 2002, pp. 1268-1274, discussion pp. 1274-1276.
Olin et al., "Postural Changes in Spinal Cord Stimulation Perceptual Thresholds", Neuromodulation, vol. 1 , No. 4, 1998, pp. 171-175.
Opsommer, E. et al. "Determination of Nerve Conduction Velocity of C-fibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.
Orstavik et al., "Pathological C-fibres in patients with a chronic painful condition", Brain (2003), 126, 567-578.
Ouyang et al., "Compression Induces Acute Demyelination and Potassium Channel Exposure in Spinal Cord", Journal of Neurotrauma 27, No. 6, Jun. 2010, 1109-1120, doi:10.1089/neu.2010.1271.
Parker et al., "Closing the Loop in Neuromodulation Therapies: Spinal Cord Evoked Compound Action Potentials During Stimulation for Pain Management (230).", 2011, In 15th Annual Meeting, North American Neuromodulation Society (p. 48). Presented at the North American Neuromodulation Society, Las Vegas.
Parker et al., "Compound Action Potentials Recorded in the Human Spinal Cord During Neurostimulation for Pain Relief", Pain, vol. 153, 2012, pp. 593-601.
Parker et al., "Electrically Evoked Compound Action Potentials Recorded From the Sheep Spinal Cord", Neuromodulation, vol. 16, 2013, pp. 295-303.
Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.
Peterson et al., "Stimulation artifact rejection in closed-loop, distributed neural interfaces", ESSCIRC, 42nd European Solid-State Circuits Conference, Lausanne, 20L6, pp. 233-235.

Rattay, "Analysis of Models for External Stimulation of Axons", IEEE Transactions on Biomedical Engineering, vol. BME-33, No. 10, Oct. 1986, pp. 974-977.
Richter et al., "EMG and SSEP Monitoring During Cervical Spinal Cord Stimulation", Journal of Neurosurgical Review 2011, Southern Academic Press, 1(S1), 2011, pp. 61-63.
Ridder et al., "Burst Spinal Cord Stimulation for Limb and Back Pain", World Neurosurgery, 2013, 9 pgs.
Rijkhoff et al., "Acute Animal Studies on the Use of Anodal Block to Reduce Urethral Resistance in Sacral Root Stimulation", IEEE Transactions on Rehabilitation Engineering, vol. 2, No. 2, 1994.
Rijkhoff et al., "Orderly Recruitment of Motoneurons in an Acute Rabbit Model", Annual International Conference of the IEEE Engineering in Medicine and Biology Society, vol. 20, No. 5, 1998.
Ross et al., "Improving Patient Experience with Spinal Cord Stimulation: Implications of Position-Related Changes in Neurostimulation", Neuromodulation 2011; e-pub ahead of print. DOI: 10.1111/j.1525-1403.2011.00407.x, 6 pages.
Roy et al., "Effects of Electrode Location on Myoelectric Conduction Velocity and Median Frequency Estimates", J. Appl. Physiol. 61 (4), 1986, pp. 1510-1517.
Sayenko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.
Schmidt et al., "Gating of tactile input from the hand", Exp Brain Res, 1990, 79, pp. 97-102.
Scott et al., "Compact Nonlinear Model of an Implantable Electrode Array for Spinal Cord Stimulation (SCS)", IEEE Transactions on Biomedical Circuits and Systems, 2014, vol. 8, No. 3, pp. 382-390.
Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.
Siegfried et al., "Bilateral Chronic Electrostimulation of Ventroposterolateral Pallidum: A New Therapeutic Approach for Alleviating All Parkinsonian Symptoms", Issue: vol. 35(6), Dec. 1994, p. 1126-1130; Copyright: Copyright © by the Congress of Neurological Surgeons; Publication Type: [Technique and Application, ISSN: 0148-396X; Accession: 00006123-199412000-00016; Keywords: Chronic deep brain stimulation, Pallidum, Parkinson's disease, Stereotactic operation.
Siegfried et al., "Intracerebral Electrode Implantation System", Journal of Neurosurgery, vol. 59, No. 2, Aug. 1983, pp. 356-3591.
Srinivasan, S "Electrode/Electrolyte Interfaces: Structure and Kinetics of Charge Transfer", Fuel Cells, 2006, Chapter 2, 67 Pages.
Stanslaski et al., "Design and Validation of a Fully Implantable, Chronic, Closed-Loop Neuromodulation Device With Concurrent Sensing and Stimulation", IEEE Transactions on Neural Systems and Rehabilitation Engineering, Jul. 2012, Date of Publication: Jan. 23, 2012, vol. 20, No. 4, pp. 410-421, DOI: 10.1109/TNSRE.2012.2183617.
Struijk, "The Extracellular Potential of a Myelinated Nerve Fiber in an Unbounded Medium and in Nerve Cuff Models", Biophysical Journal vol. 72 Jun. 1997 2457-2469.
Struijk et al, "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.
Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.
Sufka et al., "Gate Control Theory Reconsidered", Brain and Mind, 3, No. 2, 2002, pp. 277-290.
Tamura et al., "Increased Nodal Persistent Na+ Currents in Human Neuropathy and Motor Neuron Disease Estimated by Latent Addition", Clinical Neurophysiology 117, No. 11 (Nov. 2006): 2451-2458, doi:10.1016/j.clinph.2006.07.309.
Tasker, "Deep Brain Stimulation is Preferable to Thalamotomy for Tremor Suppression", Surgical Neurology, 49, No. 2, 1998, pp. 145-153.

(56) References Cited

OTHER PUBLICATIONS

Taylor et al., "Spinal Cord Stimulation for Chronic Back and Leg Pain and Failed Back Surgery Syndrome: A Systematic Review and Analysis of Prognostic Factors", Spine, vol. 30, No. 1, 2004, pp. 152-160.

Texas Instruments, "Precision, Low Power Instrumentation Amplifiers", Texas Instruments SBOS051B Oct. 1995, Revised Feb. 2005, 20 pgs.

Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.

Tronnier et al., "Magnetic Resonance Imaging with Implanted Neurostimulators: An In Vitro and In Vlvo Study", Jan. 1999, Neurosurgery, vol. 44(1), p. 118-125 (Year: 1999).

Tscherter et al., "Spatiotemporal Characterization of Rhythmic Activity in Rat Spinal Cord Slice Cultures", European Journal of Neuroscience 14, No. 2 (2001), pp. 179-190.

Van Den Berg et al., "Nerve fiber size-related block of action currents by phenytoin in mammalian nerve", Epilepsia, Nov. 1994, 35(6), pp. 1279-1288.

Villavicencio, Alan T. "Laminectomy versus Percutaneous Electrode Placement for Spinal Cord Stimulation," Neurosurgery, vol. 46 (2), Feb. 2000, pp. 399-405.

Vleggeert et al., Lankamp "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.

Woessner, "Blocking Out the Pain, Electric Nerve Block Treatments for Sciatic Neuritis", Retrieved from: http://www.practicalpainmanagement.com/pain/spine/radiculopathy/blocking-out-pain, Last updated Jan. 10, 2012.

Wolter et al., "Effects of sub-perception threshold spinal cord stimulation in neuropathic pain: A randomized controlled double-blind crossover study", European Federation of International Association for the Study of Pain Chapters, 2012, pp. 648-655.

Wu et al., "Changes in Aβ Non-nociceptive Primary Sensory Neurons in a Rat Model of Osteoarthritis Pain", Molecular Pain 6, No. 1 (Jul. 1, 2010): 37, doi:10.1186/1744-8069-6-37.

Wulfhorst et al., Textile Technology, Carl Hanser Verlag Munich 2006.

Xie et al., "Functional Changes in Dorsal Root Ganglion Cells after Chronic Nerve Constriction in the Rat", Journal of Neurophysiology 73, No. 5 (May 1, 1995): 1811-1820.

Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.

Yamada et al., "Extraction and Analysis of the Single Motor Unit F-Wave of the Median Nerve", EMG Methods for Evaluating Muscle and Nerve Function, InTech, 2012, 15 pgs.

Yearwood, T. L. "Pulse Width Programming in Spinal Cord Stimulation: a Clinical Study", Pain Physician. 2010. vol. 13, pp. 321-335.

Yingling et al., "Use of Antidromic Evoked Potentials in Placement of Dorsal Cord Disc Electrodes", Applied Neurophysiology, 1986, vol. 49, pp. 36-41.

Yuan, S. et al. "Recording monophasic action potentials using a platinum-electrode ablation catheter", Europace. Oct. 2000; 2(4):312-319.

Zhou et al., "A High Input Impedance Low Noise Integrated Front-End Amplifier for Neural Monitoring", IEEE Transactions on Biomedical Circuits and Systems, 2016, vol. 10, No. 6, pp. 1079-1086.

Extended European Search Report for European Application 18910394.8 Search Completed Oct. 7, 2021, Mailed Oct. 15, 2021, 8 pgs.

Extended European Search Report for European Application No. 16802238.2, Mailed Jan. 14, 2022, 7 Pgs.

Extended European Search Report for European Application No. 19793420.1, Search completed Dec. 6, 2021, Mailed Dec. 17, 2021, 9 Pgs.

International Search Report and Written Opinion for International Application No. PCT/AU2020/050725, Search completed Oct. 19, 2020, Mailed Oct. 19, 2020, 8 Pgs.

Parker et al., "Electrically evoked compound action potential recording in peripheral nerves", Bioeletron. Med., vol. 1, No. 1, 2018, pp. 71-83, ISSN 2059-1500.

Communication Pursuant to Article 94(3) EPC, for European Patent Application No. 14861553.7, Dated Nov. 4, 2022, 8 Pgs.

Extended European Search Report for European Application 19876581.0 Search Completed Jun. 7, 2022, Mailed Jun. 15, 2022, 7 pgs.

Extended European Search Report for European Application No. 19875139.8, Search completed Jun. 7, 2022, Mailed Jun. 15, 2022, 8 Pgs.

Extended European Search Report for European Application No. 19899138.2, Search completed Jul. 26, 2022, Mailed Aug. 3, 2022, 09 Pgs.

Islam et al., "Methods for artifact detection and removal from scalp EEG: A review", Neurophysiologie Clinique—Clinical Neurophysiology, vol. 46, No. 4, pp. 287-305, XP029804850, ISSN: 0987-7053, DOI: 10.1016/J.NEUCLI.2016.07.002, 2016.

Li et al., "Therapeutic Deep Brain Stimulation in Parkinsonian Rats Directly Influences Motor Cortex", Neuron, vol. 76, No. 5, pp. 1030-1041, XP0289601 09, ISSN: 0896-6273, 001: 10.1 016/J.NEURON.2012.09.032, 2012.

Shepherd et al., "Electrical stimulation of the auditory nerve: II. Effect of stimulus waveshape on single fibre response properties", Hearing Research, 1999, 130, 171-188.

International Search Report and Written Opinion for International Application No. PCT/AU2019/051385, Search completed Mar. 24, 2020, Mailed Mar. 24, 2020, 8 pgs.

"Percutaneous Lead Kit", St. Jude Medical Clinician's Manual, Models 3143, 3146, 3149, 3153, 3156, 3159, 3183, 3186, 3189, published Sep. 2016, 24 pages.

Abrard et al., "A time-frequency blindsignal separation methodapplicable to underdetermined mixtures of dependent sources", Signal Processing 85 (2005) 1389-1403.

Casey et al., "Separation of Mixed Audio Sources by Independent Subspace Analysis", Mitsubishi Electric Research Laboratories (2001), 8 pgs.

Jang et al, "Single Channel Signal Separation Using Time-Domain Basis Functions", IEEE Signal Processing Letters, Jun. 2003, vol. 10, No. 6, 13 pgs.

Jang et al., "A Maximum Likelihood Approach to Single-channel Source Separation", Journal of Machine Learning Research, Dec. 2003, vol. 4, pp. 1365-1392.

Laird-Wah, "Improving Spinal Cord Stimulation: Model-Based Approaches to Evoked Response Telemetry", UNSW Thesis, Aug. 2015, 279 pgs.

Mannan et al., "Identification and Removal of Physiological Artifacts From Electroencephalogram Signals: A Review", IEEE Access, May 31, 2018, vol. 6, pp. 30630-30652, https://doi.org/10.1109/ACCESS.2018.2842082.

Niazy et al., "Removal of FMRI environment artifacts from EEG data using optimal basis sets", NeuroImage, 2005, vol. 28, pp. 720-737, available online Sep. 16, 2005, doi:10.1016/j.neuroimage.2005.06.0607.

Takahashi et al, "Classification of neuronal activities from tetrode recordings using independent component analysis", Neurocomputing, (2002), vol. 49, Issues 1-4, pp. 289-298.

Zhang et al., "Automatic Artifact Removal from Electroencephalogram Data Based on A Priori Artifact Information", BioMed Research International, Aug. 25, 2015, Article ID 720450, 8 pgs., DOI: https://doi.org/10.1155/2015/720450.

METHOD AND DEVICE FOR DETECTING A NEURAL RESPONSE IN NEURAL MEASUREMENTS

CROSS-REFERENCE TO RELATED APPLICATIONS

This application is a continuation of U.S. application Ser. No. 15/527,314, filed May 16, 2017, which is a national stage of Application No. PCT/AU2015/050724, filed Nov. 17, 2015, which application claims the benefit of Australian Provisional Patent Application No. 2014904595, filed Nov. 17, 2014, the disclosures of which are incorporated herein by reference in their entireties.

TECHNICAL FIELD

The present invention relates to detection of a neural response, such as a neural response caused by a stimulus. In particular the present invention relates to detection of a compound action potential by using one or more electrodes implanted proximal to the neural pathway to obtain a neural measurement.

BACKGROUND OF THE INVENTION

Electrical neuromodulation is used or envisaged for use to treat a variety of disorders including chronic pain, Parkinson's disease, and migraine, and to restore function including but not limited to hearing and motor function. A neuromodulation system applies an electrical pulse to neural tissue in order to generate a therapeutic effect. Such a system typically comprises an implanted electrical pulse generator, and a power source such as a battery that may be rechargeable by transcutaneous inductive transfer. An electrode array is connected to the pulse generator, and is positioned close to the neural pathway(s) of interest. A suitable electrical pulse applied to the neural pathway by an electrode causes the depolarisation of neurons, which generates propagating action potentials whether antidromic, orthodromic, or both, to achieve the therapeutic effect.

When used to relieve chronic pain for example, the electrical pulse is applied to the dorsal column (DC) of the spinal cord and the electrode array is positioned in the dorsal epidural space. The dorsal column fibres being stimulated in this way inhibit the transmission of pain signals through that segment in the spinal cord to the brain.

In general, the electrical stimulus generated in a neuromodulation system triggers a neural action potential which then has either an inhibitory or excitatory effect. Inhibitory effects can be used to modulate an undesired process such as the transmission of pain, or excitatory effects can be used to cause a desired effect such as the contraction of a muscle or stimulation of the auditory nerve.

The action potentials generated among a large number of fibres sum to form a compound action potential (CAP). The CAP is the sum of responses from a large number of single fibre action potentials. When a CAP is electrically recorded, the measurement comprises the result of a large number of different fibres depolarising. The propagation velocity is determined largely by the fibre diameter and for large myelinated fibres as found in the dorsal root entry zone (DREZ) and nearby dorsal column the velocity can be over 60 ms$^{-1}$. The CAP generated from the firing of a group of similar fibres is measured as a positive peak P1 in the recorded potential, then a negative peak N1, followed by a second positive peak P2. This is caused by the region of activation passing the recording electrode as the action potentials propagate along the individual fibres, producing the typical three-peaked response profile. Depending on stimulus polarity and the sense electrode configuration, the measured profile of some CAPs may be of reversed polarity, with two negative peaks and one positive peak.

To better understand the effects of neuromodulation and/or other neural stimuli, and for example to provide a stimulator controlled by neural response feedback, it is desirable to accurately detect a CAP resulting from the stimulus. Evoked responses are less difficult to detect when they appear later in time than the artifact, or when the signal-to-noise ratio is sufficiently high. The artifact is often restricted to a time of 1-2 ms after the stimulus and so, provided the neural response is detected after this time window, a response measurement can be more easily obtained. This is the case in surgical monitoring where there are large distances (e.g. more than 12 cm for nerves conducting at 60 ms$^{-1}$) between the stimulating and recording electrodes so that the propagation time from the stimulus site to the recording electrodes exceeds 2 ms.

To characterize the responses from the dorsal columns, high stimulation currents and close proximity between electrodes are required, and therefore in such situations the measurement process must overcome artifact directly. However, this can be a difficult task as an observed CAP signal component in the neural measurement will typically have a maximum amplitude in the range of microvolts. In contrast a stimulus applied to evoke the CAP is typically several volts and results in electrode artifact, which manifests in the neural measurement as a decaying output of several millivolts partly or wholly contemporaneously with the CAP signal, presenting a significant obstacle to isolating or even detecting the much smaller CAP signal of interest.

For example, to resolve a 10 uV CAP with 1 uV resolution in the presence of an input 5 V stimulus requires an amplifier with a dynamic range of 134 dB, which is impractical in implant systems. As the neural response can be contemporaneous with the stimulus and/or the stimulus artefact, CAP measurements present a difficult challenge of measurement amplifier design. In practice, many non-ideal aspects of a circuit lead to artefact, and as these mostly have a decaying exponential appearance that can be of positive or negative polarity, their identification and elimination can be laborious.

The difficulty of this problem is further exacerbated when attempting to implement CAP detection in an implanted device. Typical implants have a power budget which permits a limited number, for example in the hundreds or low thousands, of processor instructions per stimulus, in order to maintain a desired battery lifetime. Accordingly, if a CAP detector for an implanted device is to be used regularly (e.g. once a second), then the detector should preferably consume only a small fraction of the power budget and thus desirably should require only in the tens of processor instructions in order to complete its task.

Approaches proposed for obtaining a neural measurement include that described in International Patent Publication No. WO 2012/155183. Approaches to identifying whether a neural response is present in a neural measurement include the program method described in International Patent Publication No. WO 2012/155190.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides a method for processing a neural measurement obtained in the presence of noise, in order to detect whether a locally evoked neural response is present in the neural measurement, the method comprising:
  obtaining a first neural measurement from a first sense electrode;
  obtaining a contemporaneous second neural measurement from a second sense electrode spaced apart from the first electrode along a neural pathway of the neural response;
  determining a neural response decay, being a measure of the decay in the neural response from the first sense electrode to the second sense electrode;
  calculating a ratio of the neural response decay to an amplitude normalising term; and
  determining from the ratio whether a locally evoked neural response is present in the neural measurement.

According to a second aspect the present invention provides an implantable device for processing a neural measurement obtained in the presence of noise, in order to detect whether a locally evoked neural response is present in the neural measurement, the device comprising:
  measurement circuitry for obtaining a first neural measurement from a first sense electrode, and for contemporaneously obtaining a second neural response measurement from a second sense electrode spaced apart from the first electrode along a neural pathway of the neural response; and
  a processor configured to determine a neural response decay, being a measure of the decay in the neural response from the first sense electrode to the second sense electrode; the processor further configured to calculate a ratio of the neural response decay to an amplitude normalising term; and the processor further configured to determine from the ratio whether a locally evoked neural response is present in the neural measurement.

According to a third aspect the present invention provides a non-transitory computer readable medium for processing a neural measurement obtained in the presence of noise, in order to detect whether a locally evoked neural response is present in the neural measurement, comprising instructions which, when executed by one or more processors, causes performance of the following:
  obtaining a first neural measurement from a first sense electrode;
  obtaining a contemporaneous second neural measurement from a second sense electrode spaced apart from the first electrode along a neural pathway of the neural response;
  determining a neural response decay, being a measure of the decay in the neural response from the first sense electrode to the second sense electrode;
  calculating a ratio of the neural response decay to an amplitude normalising term; and
  determining from the ratio whether a locally evoked neural response is present in the neural measurement.

The present invention recognises that a locally evoked neural response, being a neural response evoked at a site close to the sense electrodes, such as within 100 mm or less, will undergo a decay in the CAP signal amplitude as it propagates away from the stimulus site, due at least in part to a spreading in time of the responses of individual fibres having differing conduction velocity, and a change in depth of individual fibres within the spinal cord as the CAP propagates. This is in contrast to a distally evoked response, which will present a substantially constant neural signal strength to both sense electrodes. Accordingly the present invention provides a way to determine whether a sensed neural response has been locally evoked or distally evoked. Such a capability may thus be used for example to characterise the performance of a local electrical stimulus regime, without corruption from noise such as coexisting neural responses occurring on the neural pathway due to the subject's independent motor activity and/or sensory stimulation. Such distally evoked responses give rise to considerable neural activity and, without a means for distinguishing between locally evoked responses and distally evoked responses, distally evoked response noise can lead to a conclusion that locally applied electrical stimuli are performing appropriately when in fact they are not.

The neural response decay may in some embodiments be determined by determining a first amplitude of the first neural measurement, determining a second amplitude of the second neural measurement, and calculating a difference between the first amplitude and the second amplitude. In such embodiments, the CAP amplitude may be determined in any suitable manner, for example in accordance with the teachings of Australian Provisional Patent Application No. 2013904519, the content of which is incorporated herein by reference. Additionally or alternatively, the neural response decay may in some embodiments be determined by determining a first width of the first neural measurement, determining a second width of the second neural measurement, and calculating a difference between the first width and second width. Still further embodiments may determine the ratio as being a ratio of the amplitude (or energy, power of other strength measure) of the first neural measurement to the amplitude (or energy, power of other strength measure) of the second neural measurement.

The amplitude normalising term may in some embodiments of the invention comprise a sum of the first amplitude and second amplitude, a sum of scalar or other variants of the first amplitude and second amplitude, a scalar or other variant of the first amplitude alone, or a scalar or other variant of the second amplitude alone. The present invention recognises that such normalisation of the difference value is an important element of detecting neural responses because of the propensity of spinal cord electrode arrays to move relative to the spinal cord and alter the electrode-to-fibre distance, and because of the impact of the electrode-to-fibre distance upon both (i) the amplitude of the response evoked by a given stimulus, and (ii) the amplitude of a neural measurement obtained from a given neural response.

The first and second amplitudes are preferably determined at a moment of the respective measurement corresponding to an expected occurrence of a neural response to be detected, as determined by reference to an electrical stimulus timing and a distance from the stimulus site to the respective sense electrode.

In some embodiments the measurement is obtained in accordance with the teachings of International Patent Publication No. WO 2012/155183, by the present applicant.

In some embodiments the detector output is used in a closed loop feedback circuit to control neuromodulation, for example in conjunction with the techniques of International Patent Publication No. WO 2012/155188, by the present applicant, the content of which is incorporated herein by reference. Such embodiments may thus effect feedback control of electrical stimuli with improved resistance to corruption by the patient's independent motor activity and/or peripheral stimuli.

In some embodiments the method may be repeated in order to obtain a plurality of ratios resulting from repeated application of a given stimulus. The plurality of ratios may then give a probabilistic indication of the neural response decay to improve the determination of whether a locally evoked response is present.

In some embodiments, the method may be performed repeatedly, regularly or substantially continuously, in order to monitor changes in the ratio which occur over time, for example in response to postural changes of the subject, movement of the subject, peripheral stimuli experienced by the subject, electrode lead movement, injury or disease affecting the neural pathway, or a change in efficacy of a therapy such as medication.

In some embodiments the method of the present invention may further comprise the step of detecting whether any neural activity is present. Such embodiments recognise that insufficiently suppressed stimulus artefact also decays with distance from the stimulus site and the ratio may thus give a false positive indication that a locally evoked response is present, when in fact only artefact is present. By providing a separate step of detecting whether neural activity is present, such embodiments may provide improve performance in embodiments in which stimulus artefact is inadequately or not suppressed. Such embodiments may comprise a signal quality indicator configured to assess the neural measurement(s) in order to determine whether a signal appears to be a CAP, and if not to exclude the measurement from further processing.

In some embodiments, a contemporaneous third or additional neural measurement may be obtained from a third or additional sense electrode(s) spaced apart from the first and second electrodes along a neural pathway of the neural response. Such embodiments may be used for three or more point fitting of a decay coefficient of the observed response, for use as a determinant of whether an observed response has been locally evoked.

BRIEF DESCRIPTION OF THE DRAWINGS

An example of the invention will now be described with reference to the accompanying drawings, in which.

DESCRIPTION OF THE PREFERRED EMBODIMENTS

Figure 1:
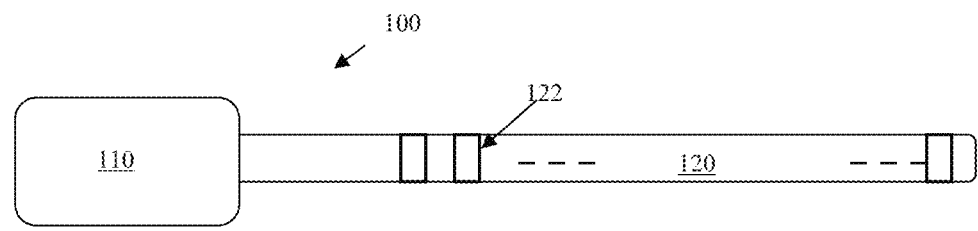
FIG. 1 illustrates an implantable device suitable for implementing the present invention.

FIG. 1 illustrates an implantable device 100 suitable for implementing the present invention. Device 100 comprises an implanted control unit 110, which controls application of neural stimuli, and controls a measurement process for obtaining a measurement of a neural response evoked by the stimuli from each of a plurality of electrodes. The control unit 110 includes a processor and a storage memory (or other storage device(s), not shown) for carrying out the method of the present embodiment of the invention. Device 100 further comprises an electrode array 120 consisting of a linear array of electrodes 122, each of which may be selectively used as either the stimulus electrode or sense electrode, or both.

Figure 2:
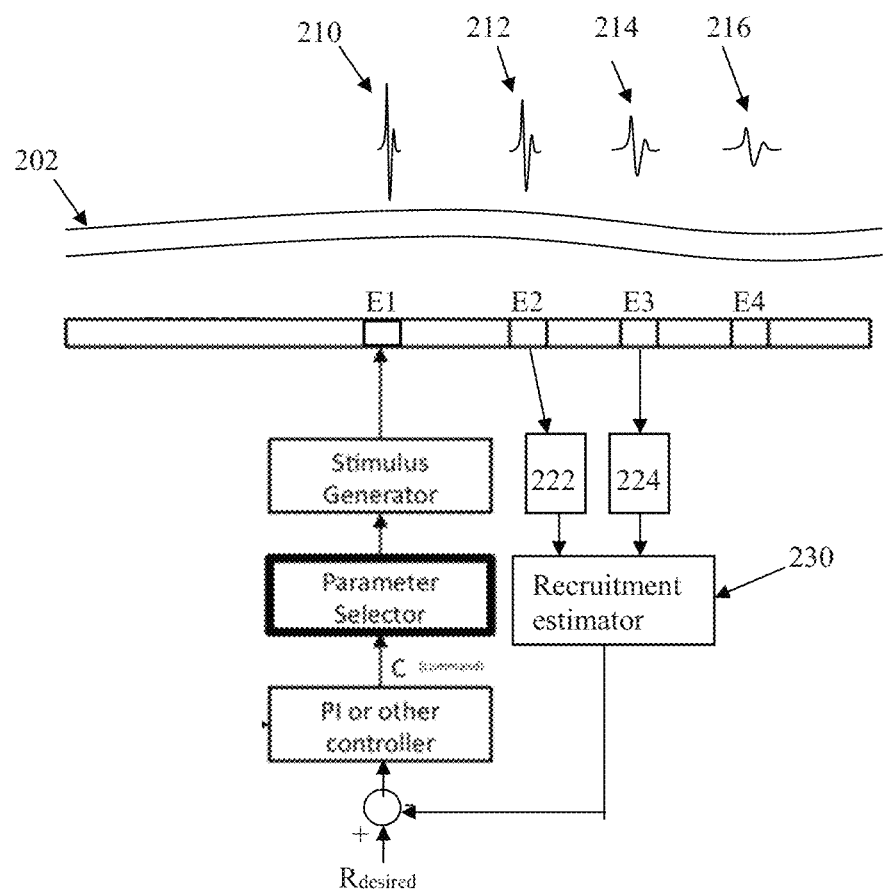
FIG. 2 is a schematic of a feedback controller to effect stimulus control in response to neural recruitment in accordance with one embodiment of the present invention.

FIG. 2 is a schematic of a feedback controller implemented by the control unit 110, based on recruitment. An important component of such feedback control is a recruitment estimator 230, which performs the difficult task of detecting whether an evoked neural response is present in a neural measurement as a result of the electrical stimulus.

In this embodiment, electrical stimuli are delivered to the spinal cord 202 by one or more stimulus electrodes denoted E1 in FIG. 2. A desired degree of recruitment, $R_{desired}$, is input by the user or by a setting made by a clinician when fitting the device or by any other suitable means for defining desired recruitment. $R_{desired}$ is processed by a controller and selector and passed to a stimulus generator which generates a stimulus to be delivered to the neural tissue by E1. As will be appreciated while only a single stimulus electrode E1 is shown in FIG. 2, a bipolar, monopolar or tripolar stimulus may be applied in conjunction with other stimulus electrodes, not shown. At the stimulus site adjacent to E1 within the spinal cord 202, a neural response is evoked by the stimulus.

The neural response evoked by the stimulus at E1 is a compound response comprising the individual responses evoked in a number of fibres, and takes a form shown at 210. The evoked response 210 propagates along the recruited fibres within the spinal cord 202 away from the stimulus site adjacent to E1, and in so doing the form or morphology of the compound response alters or decays. Without intending to be limited by theory, the decay in the neural response as it travels is at least in part due to a spreading of the compound response resulting from each recruited fibre having a conduction velocity which differs from the conduction velocity of other recruited fibres, and the variation in depth of the recruited fibres within the cord 202 at different positions along the cord. At a time $t_2$ the compound response passes sense electrode E2 and is recorded as having an amplitude and duration indicated at 212, which differs from the form of the response at 210 in that response 212 is of reduced amplitude and greater width or duration. At a later time $t_3$, after undergoing further spreading and decay, the compound response passes sense electrode E3 and is recorded as having an amplitude and duration indicated at 214. Observed response 214 is of lesser amplitude but greater duration then observed response 212. Similarly, at a later time $t_4$, after undergoing further spreading and decay, the compound response passes electrode E4 and is recorded as having a further decreased amplitude and increased duration as indicated at 216.

It is to be appreciated that the form of each observed response, as shown at 210, 212, 214 and 216, is illustrative. The decay and spreading observed in any neural response will depend at least upon the characteristics of the fibre population actually recruited by the stimulus, the neurophysiology of the subject, and the distance of the electrodes from the fibres.

In accordance with the present invention, electrodes E2 and E3 are used to obtain a first measurement 212 and a second measurement 214 of the neural response evoked by the stimulus, via measurement circuitry 222, 224 respectively. The evoked CAP measurements in this embodiment are made by use of the neural response measurement techniques set out in International Patent Publication No. WO2012/155183, with two data channels recording simultaneous data from the two electrodes E2 and E3.

Applying a filter with optimized frequency and delay on each channel, in accordance with the teachings of Australian Provisional Patent Application No. 2013904519, the amplitude of the signals on each channel are determined and denoted as a pair of measurements CH1, CH2. Such amplitude measurement pairs are obtained repeatedly over time for each applied stimuli. For each pair of measurements, a normalized neural response decay value R is determined as follows:

$$R = \frac{CH1 - CH2}{CH1 + CH2}$$

Figure 3:
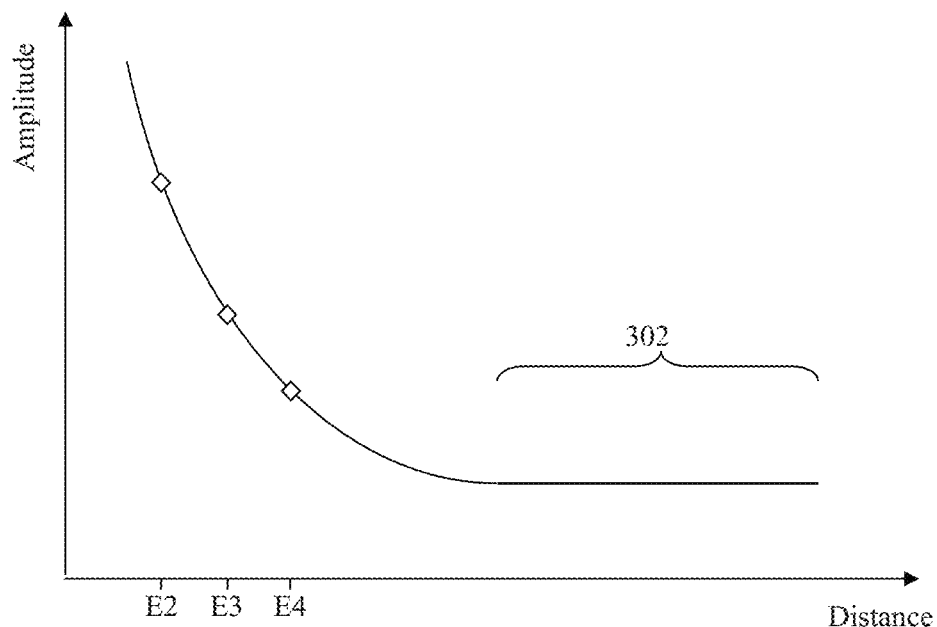
FIG. 3 illustrates the reduction in observed amplitude of an evoked neural response with increasing distance from the stimulus site.

FIG. 3 illustrates the reduction in observed amplitude of an evoked neural response with increasing distance from the stimulus site. As can be seen the absolute difference between adjacent electrode recordings is larger when closer to the stimulus site, hence the selection of E2 and E3 as sense electrodes in this embodiment, however other electrode pairs such as E3 and E4 or E2 and E4 may be used in alternative embodiments of the present invention. Once sufficiently distant from the stimulus site which depending on the patient may be around 100 mm from the stimulus, and as indicated at 302, the amplitude remains at a constant non-zero level due to the nature of neural propagation. Thus, if a neural response is evoked at such a distance or further away from the sense electrodes, the observed amplitudes will be equal at each electrode and the value of R will be zero (assuming no noise), or randomly spread in the presence of noise. On the other hand, when a neural response is evoked locally to and a constant distance from the sense electrodes E2 and E3, as is the case during effective stimulation from E1, R will take a constant non-zero value in the absence of noise, or will be distributed about that non-zero value in the presence of noise in a manner distinguishable from the values of R in the region 302.

Figure 4A:
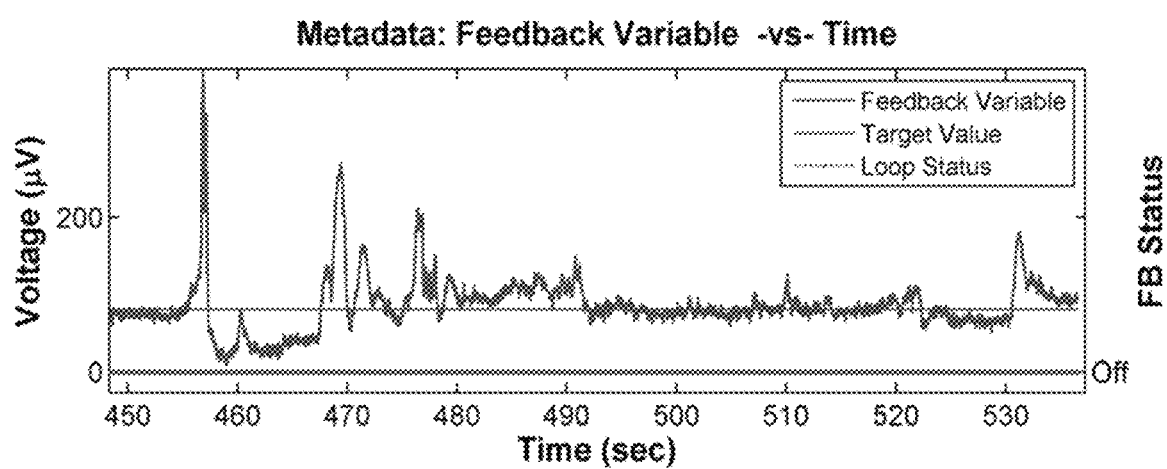
FIG. 4a illustrates the amplitude of observed neural responses of a first patient.
Figure 4B:
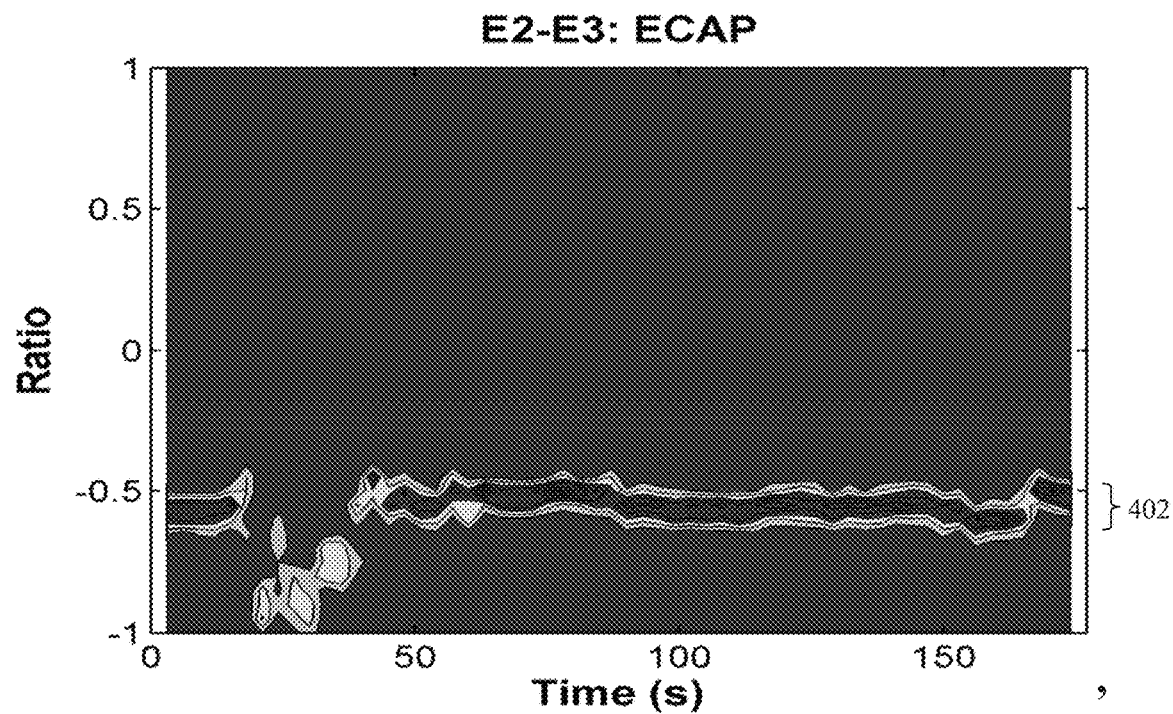
FIG. 4b is a time series of histograms of neural response decay values (R values) derived from FIG. 4a, FIG. 4c illustrates a single histogram of signal, and noise, respectively, from the same patient

FIG. 4a illustrates the amplitude of observed neural responses from a patient over a period of about 90 seconds. As can be seen, the feedback variable, being the response amplitude sensed by electrode E2, varies considerably over time for example with changes in user posture, motor activity (movement), and peripheral sensory input. Similar data (not shown) is obtained simultaneously from a second electrode E3 spaced further away from the stimulus site E1 than the first electrode E2. In accordance with the present embodiment, during this time period E1 repeatedly delivered a stimulus, and R was determined for every iteration. A histogram was then built of the calculated values of R within a 3 second interval. This is repeated in the next 3 second interval to build a further histogram, with many such histograms being built over an extended period to generate the data shown in FIG. 4b. In this case of a locally evoked response, a band 402 can be seen in FIG. 4b, where most of the ratios (R values) lie. In the present embodiments the measurement circuitry 222, 224 have differing offsets so that the curve of FIG. 3 is not followed, and in particular in the present embodiments this results in the Ratio taking a negative value despite what might be expected from FIG. 3 if the measurements had no offset. However the present invention is advantageous in this regard as it is the tightness or existence of a band which can be determined, irrespective of the position of the band, allowing such measurement offsets to be retained for measurement optimisation. In cases where the measurements have no offset, it can be deduced from FIG. 3 that Ri=0 indicates $CH_{1i}=CH_{2i}$, while Ri=1 indicates that $CH_{1i}>>CH_{2i}$. In this embodiment the dominant value of Ri is around −0.55, as seen in FIG. 4b. This band is then deemed to define the range in which an amplitude measurement is considered valid for this patient, so that an observed response which produces an R in this range, or multiple observed responses which produce an averaged R in this range, is deemed to have been a locally evoked neural response and not a distally evoked neural response.

Figure 4C:
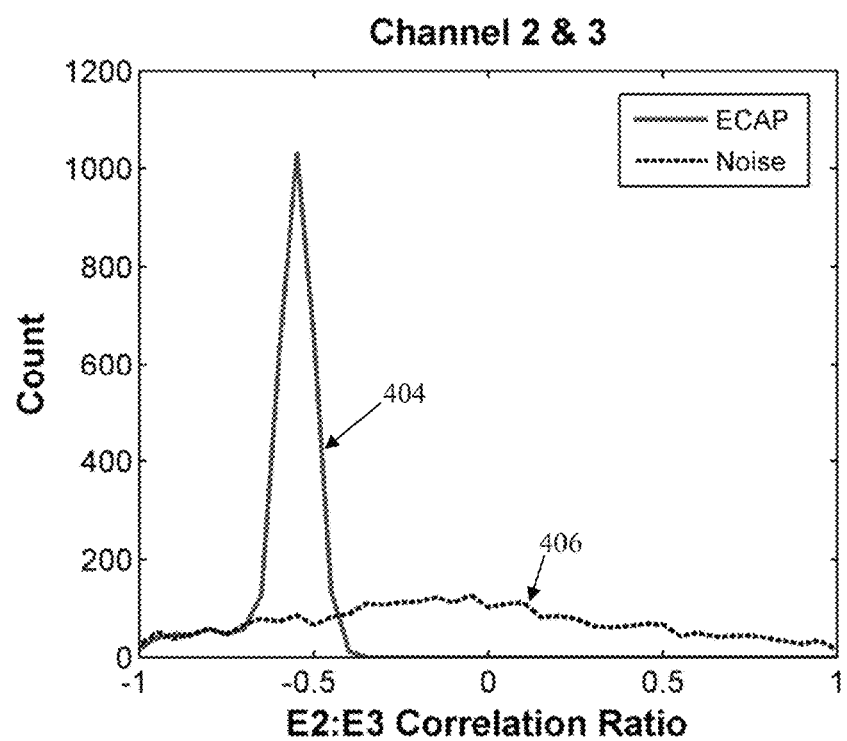
FIG. 4d illustrates the time series of the R histograms obtained in the absence of any locally evoked signals.

FIG. 4c also illustrates a histogram 406 of R which was obtained by making multiple measurements each at a time when no response was locally evoked. Histogram 406 illustrates that when measuring random noise or distally evoked neural signals, while they may occasionally produce an R within the band 402 they will not be consistently within it.

Figure 4D:
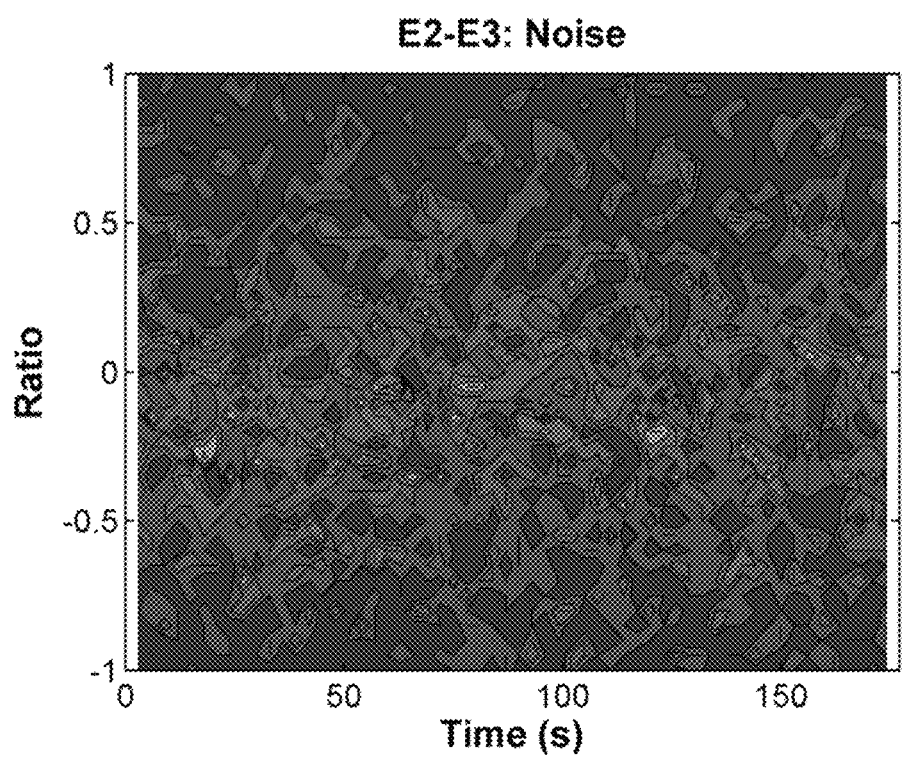

FIG. 4d illustrates the time series of the R histograms 406 obtained in the absence of any locally evoked signals. As can be seen in FIG. 4d, even though it is not known whether the sense electrodes are sensing distally evoked neural responses or merely noise, either situation is clearly differentiated from the tightly banded R data produced by locally evoked responses as shown in FIG. 4b. This shows that noise (which could comprise ascending or descending neural signals of remote origin, i.e. originating at the periphery or at the brain or otherwise originating more than a few centimetres away from the measurement electrodes) is not correlated and any neural activity is not synchronised to the stimulus. Thus the present invention provides a means by which to differentiate between a locally evoked CAP (e.g evoked by application of an electrical stimulus from an adjacent electrode) and a distally originating CAP (e.g. a CAP evoked by brain activity, reflex activity or peripheral sensory inputs).

This technique requires the clinician to calibrate the boundary of range 402 or the like for each patient, by performing a feedback experiment to determine the required band for that patient within which the device is accurately measuring a locally evoked CAP and not a distally evoked response.

Figure 5A:
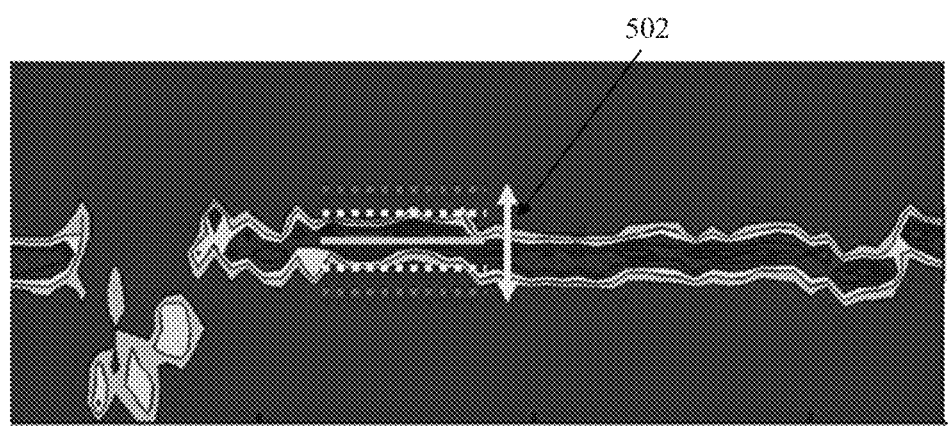
FIG. 5a illustrates selection of the upper and lower boundaries of an inclusion criterion.
Figure 5B:
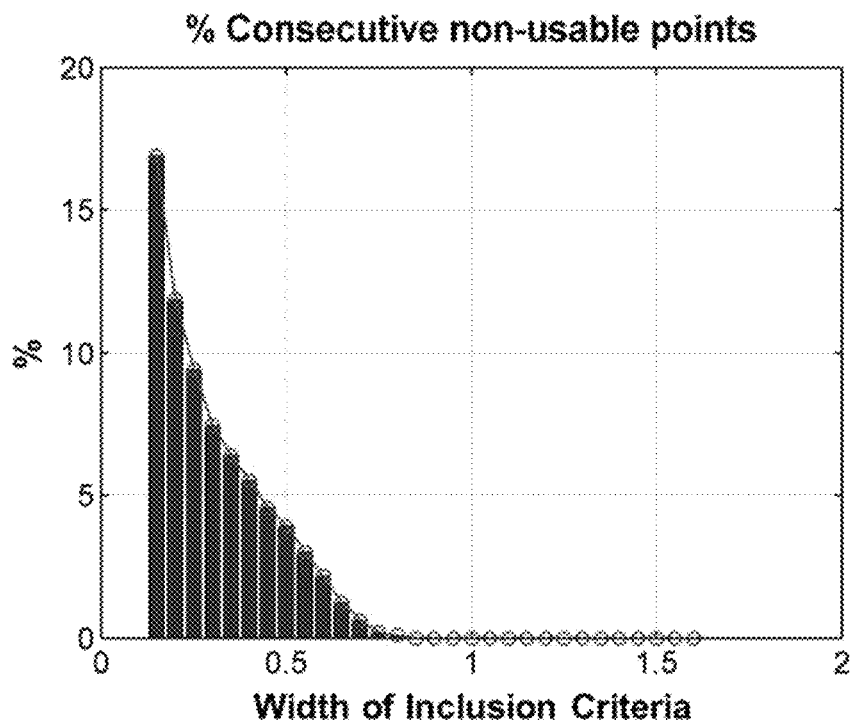
FIG. 5b illustrates for each width setting the percentage of consecutive non-usable points.

The selection of the upper and lower boundaries of range 402 was further investigated. FIG. 5a illustrates the data of FIG. 4b with a number of candidate ranges illustrated, as indicated at 502. The range 502 was centred about the mean value of R, and the width of the range 502 was varied in increments of 0.05. FIG. 5b illustrates, for each width setting of range 502, the percentage of consecutive non-usable points, being those points for which it is determined that the amplitude calculated is not due to an evoked CAP, which arise for that inclusion criteria.

Figure 6A:
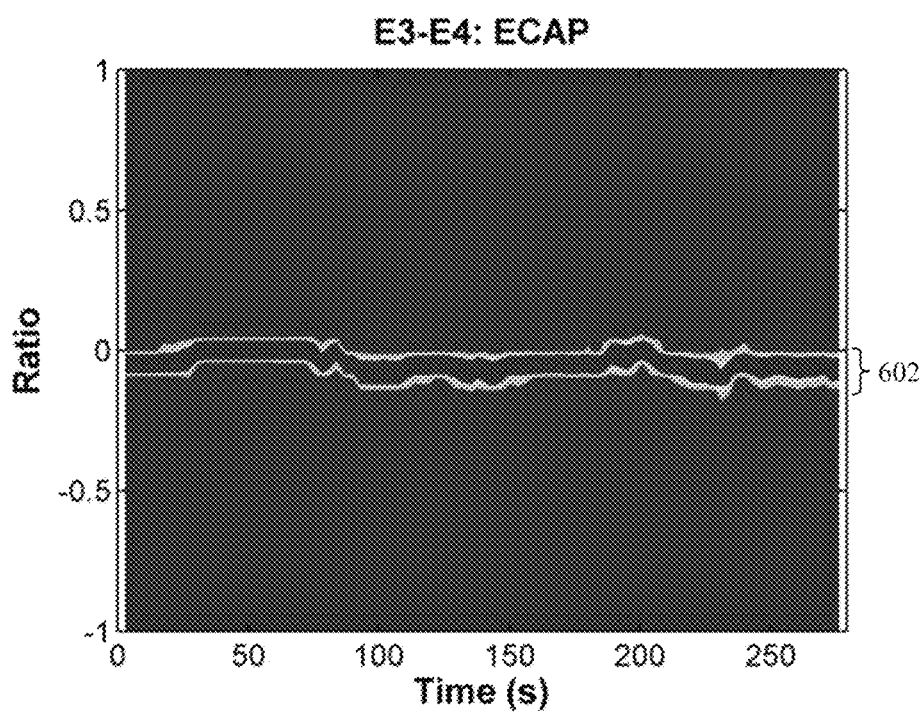
FIG. 6a is a time series of histograms of R values for evoked response signals for a second patient.
Figure 6B:
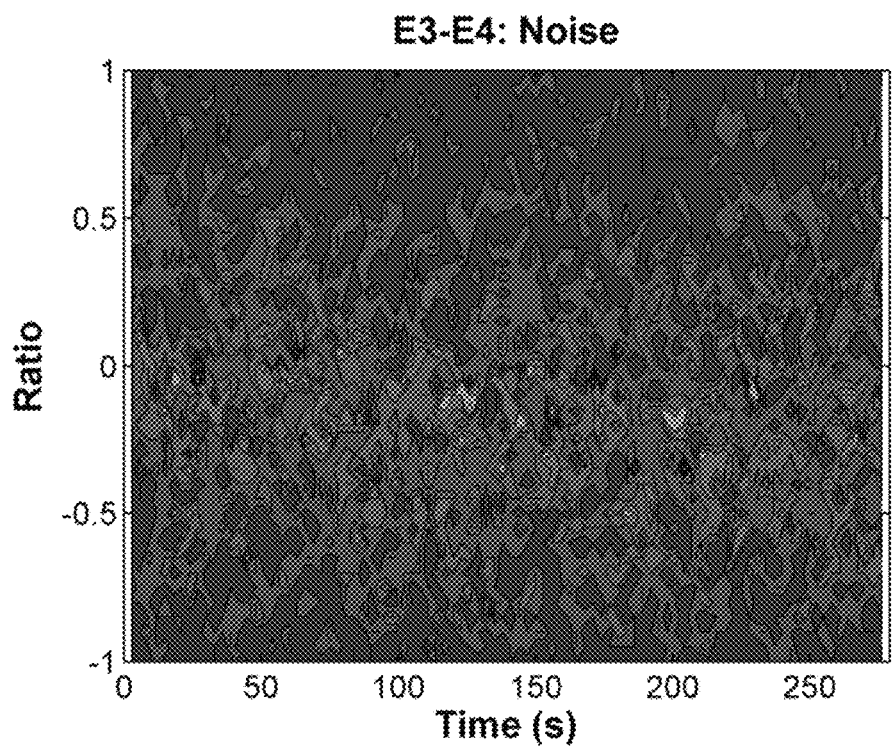
FIG. 6b is a time series of histograms for the same patient in the presence of noise only.
Figure 6C:
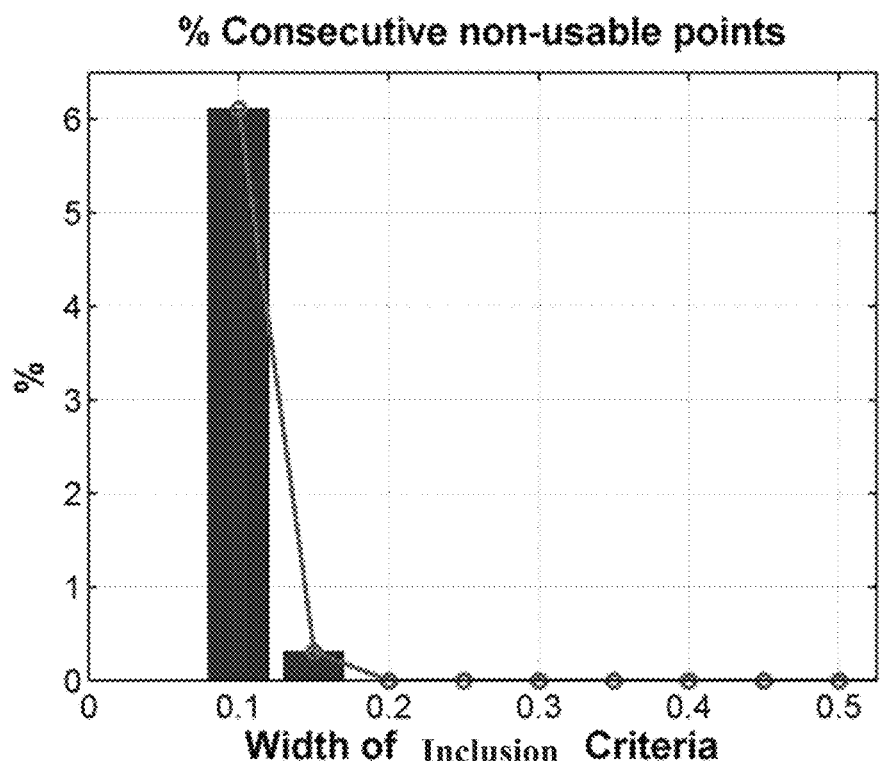
FIG. 6c illustrates the performance of differing inclusion criteria.

It is further noted that, given the variability from one patient to the next in the implantation site, electrode to fibre distance, and other parameters, the absolute and relative response amplitudes observed can vary considerably between patients. FIG. 4a shows a typical response amplitude of around 100 µV, whereas FIG. 6a illustrates data from a patient for whom the typical response amplitude was around 1,300 µV. FIG. 6a shows that a patient for whom large response measurements (>100 µV) are obtained, gives a sharper histogram and a narrower band 602, as compared to the band 402 in FIG. 4b. However, the patient of FIG. 6a exhibited a slower decay of neural response between the two electrodes (E3 and E4 in this instance), so that the R values are located much closer to zero. As can be seen with reference to FIG. 6b, the distributions of R values obtained in the presence of noise only can be easily distinguished from the tightly clustered data of FIG. 6a. FIG. 6c, illustrating the performance of differing inclusion criteria for range 602, also illustrates the improved sharpness of the histogram for the patient of FIG. 6 as compared to the patient of FIG. 4. This likely indicates not only that the original signals were smaller, but also that a higher proportion of the amplitudes measured for the patient of FIG. 6 contained neural signals.

Figure 7A:
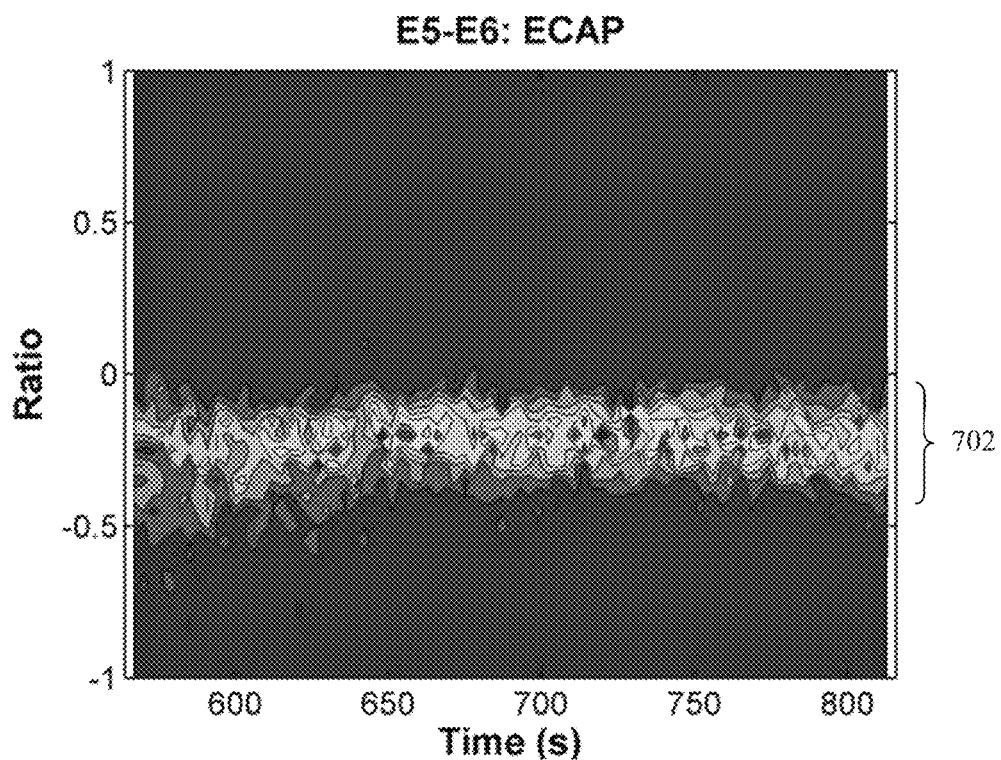
FIG. 7a is a time series of histograms of R values for evoked response signals of a third patient.
Figure 7B:
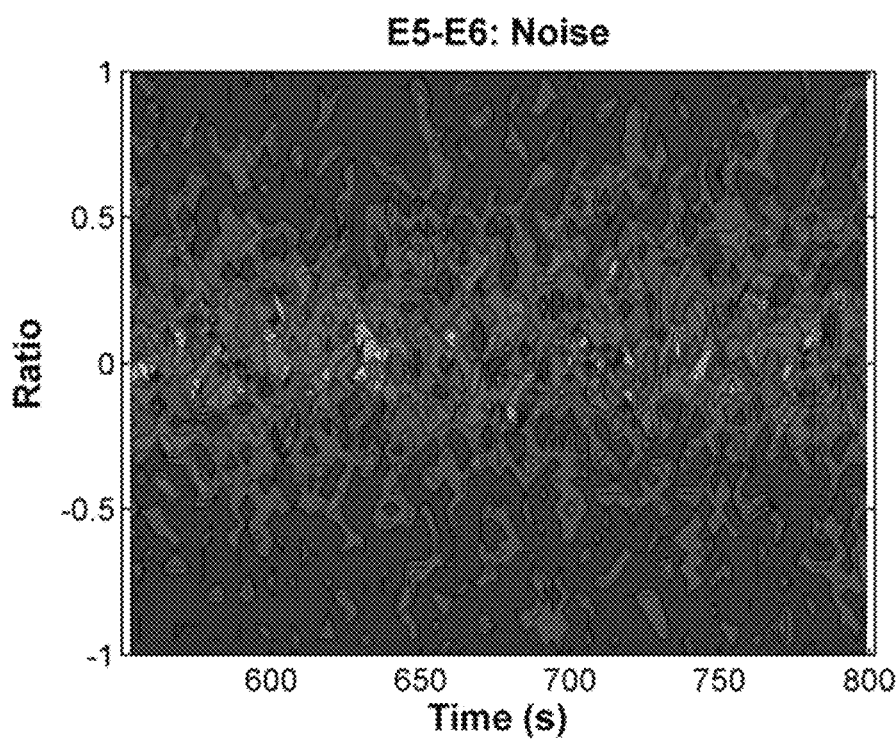
FIG. 7b illustrates the histogram of R values obtained in the presence of noise only for the same patient.
Figure 7C:
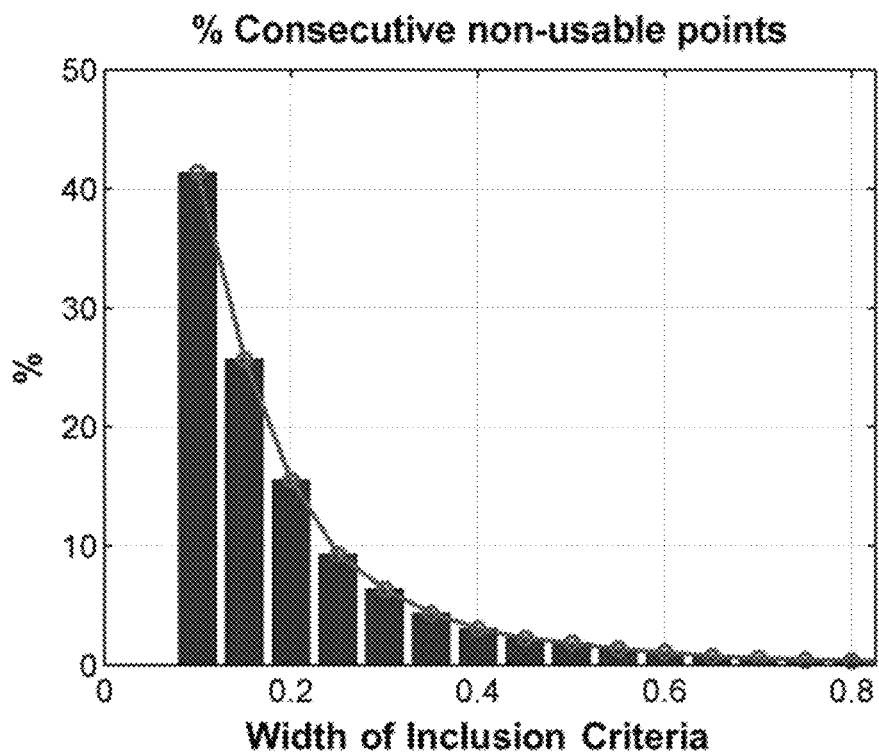
FIG. 7c illustrates the performance of differing inclusion criteria.

FIG. 7a illustrates R data for a patient for whom the amplitude of the measured responses to electrical stimuli were much smaller, only around 30 µV. As can be seen, the smaller absolute amplitudes result in a broader histogram 702, which is nevertheless clearly distinguishable from the noise-only histograms shown in FIG. 7b. FIG. 7c, illustrating the performance of differing inclusion criteria for range 702, also illustrates the wider spread of the histogram for the patient of FIG. 7 as compared to the respective patients of FIGS. 4 and 6.

Figure 8:
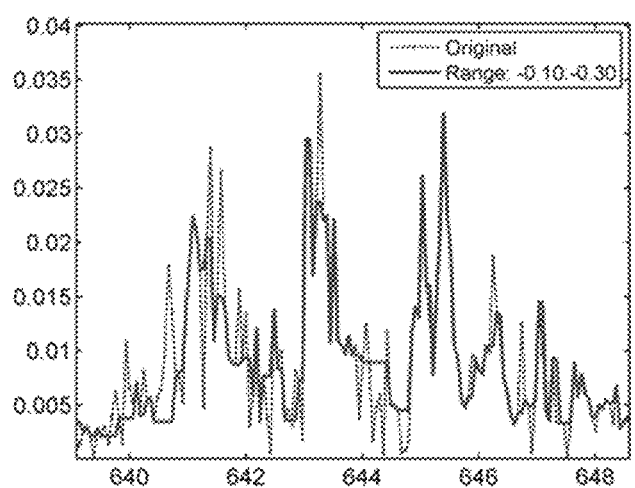
FIG. 8 illustrates rejection of neural measurements using the inclusion criteria.

FIG. 7c indicates that an inclusion criteria of 0.2, spanning a range of R values of −0.1 to −0.3, will return a false negative for about 15% of response measurements. FIG. 8 illustrates rejection of neural measurements using the inclusion criteria, by rejecting those whose R values fall outside of the set band. In particular FIG. 8 is an extract of the neural response amplitudes returned from one of the electrodes, with the dotted trace indicating the original amplitude values, and the solid trace indicating the output once those measurements deemed to be false measurements by the inclusion criteria are excluded. As expected, about 15% of measurements are rejected with the inclusion criteria set to such values. This illustrates that even for a patient from whom very small (~30 µV) response amplitudes are obtained, the method of the present embodiment is capable of identifying locally evoked neural responses with a useful degree of selectivity.

Figure 9A:
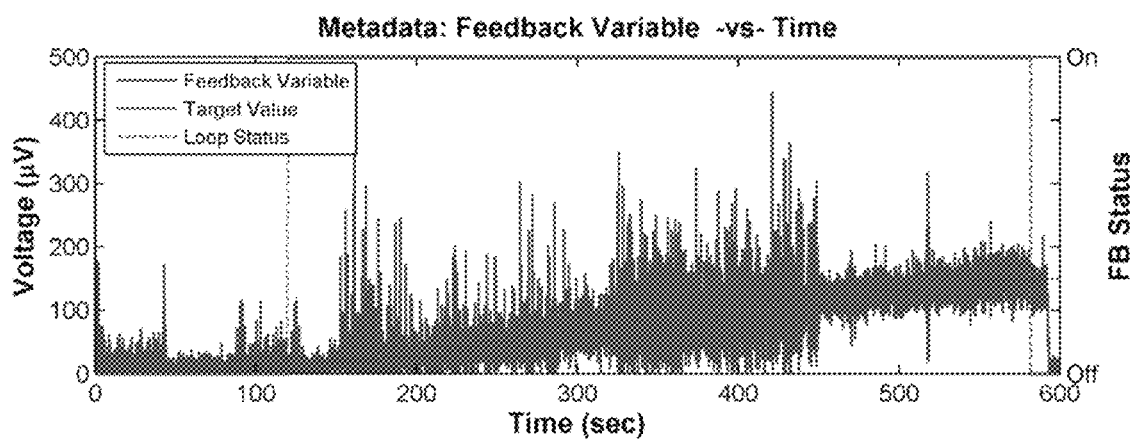
FIG. 9a is a plot of neural amplitude response data from a fourth patient.

The effect of neural response amplitude upon the band of R values was investigated. FIG. 9a is a plot of neural amplitude response data obtained over a 600 second period, with the target value (desired neural response amplitude) being stepped upwards progressively from about 100 seconds to 600 seconds, and the observed neural response amplitude (the feedback variable) rising similarly, albeit with typical variations from noise, posture, etc.

Figure 9B:
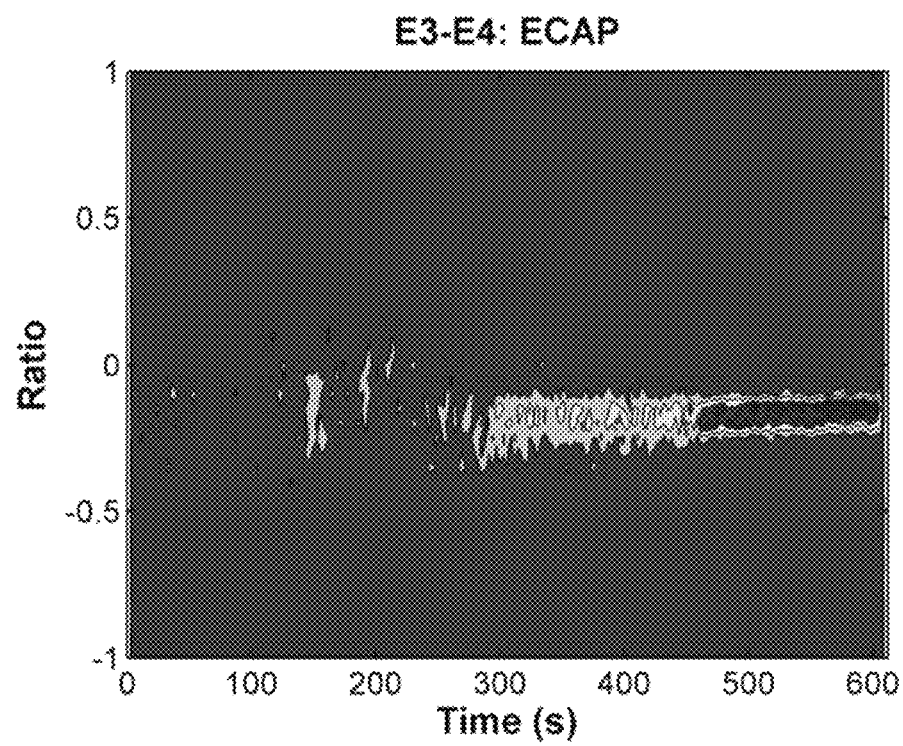
FIG. 9b is a plot of the R data obtained from FIG. 9a, and FIG. 9c is a plot of the R data obtained from noise during the same period of time.
Figure 9C:
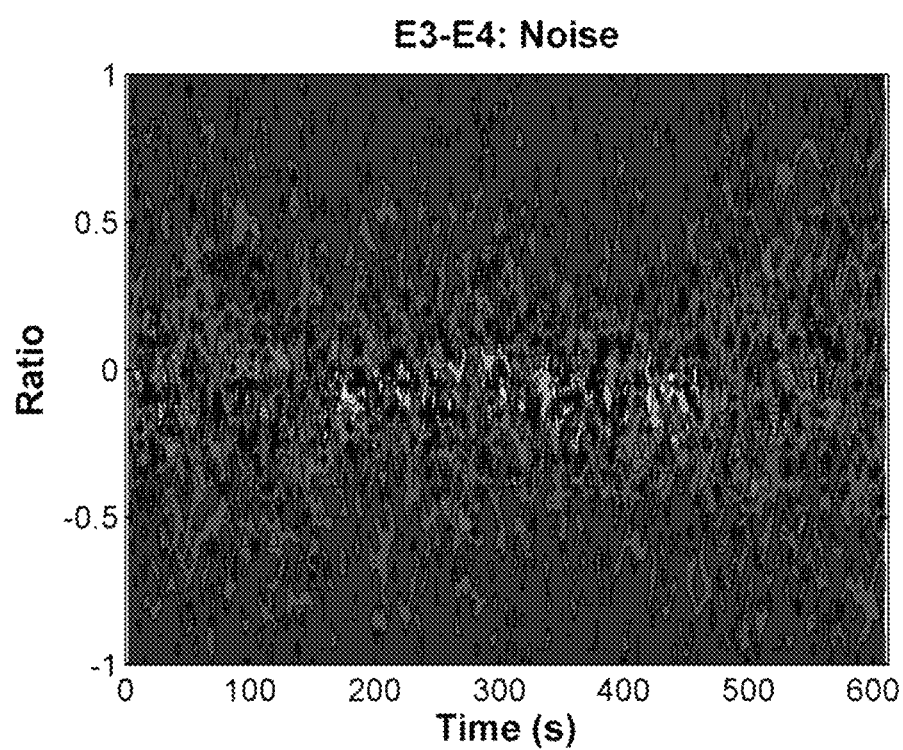

FIG. 9b is a plot of the R data obtained from the E3 and E4 electrodes during the period portrayed in FIG. 9a. As can be seen, the effect of increasing the stimulus current and thereby increasing the neural response amplitude is to increase the amplitude of the histogram, but this makes no difference to the centre position (mean R value) of the histogram. FIG. 9c illustrates noise data obtained during the same period but at times between stimuli when a locally evoked response is not expected to arise, illustrating that distally evoked responses continue to be distinguishable from a locally evoked response even with varying stimulus amplitude.

The present embodiments assume that the energy/amplitude ratio of the CAP as it propagates across electrodes is consistently within a certain range for each patient. However, alternative embodiments may take measures which allow for variations in the energy/amplitude ratio. For example, such alternative embodiments may implement a low resolution sliding time window and histogram calculation to determine if the peak has shifted.

The present embodiment also assumes that what the estimator 230 picks up is in fact a CAP most of the time. In alternative embodiments, where it is possible that a tight histogram of R values might be returned due to the presence of a constant artefact on both channels rather than due to the presence of a decaying neural response, a signal quality indicator may be integrated in order to exclude measurement pairs which are not of the typical three lobed shape of a neural response, for example.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

The invention claimed is:

1. A method for detecting locally evoked neural responses in neural measurements obtained in the presence of distally evoked neural responses, the method comprising:
   applying, by an implantable device, an electrical stimulus to a neural pathway;
   obtaining, by the implantable device, a first neural measurement from a first sense electrode coupled to the implantable device;
   obtaining, by the implantable device, a contemporaneous second neural measurement from a second sense electrode coupled to the implantable device and spaced apart from the first electrode along the neural pathway;
   determining, by the implantable device, a neural response decay, the neural response decay being a measure of decay in a neural response from the first sense electrode to the second sense electrode, from the first neural measurement and the second neural measurement;

determining, by the implantable device, from the neural response decay whether a locally evoked neural response is present in the neural measurements; and applying, by the implantable device, neurostimulation in response to the determining from the neural response decay whether a locally evoked neural response is present in the neural measurements.

2. The method of claim 1, wherein the determined presence of the locally evoked neural response is used to characterize the performance of a local electrical stimulus regime.

3. The method of claim 1, wherein the neural response decay is determined by determining a first amplitude of the first neural measurement, determining a second amplitude of the second neural measurement, and calculating a difference between the first amplitude and the second amplitude.

4. The method of claim 1, wherein the neural response decay is determined by determining a first width of the first neural measurement, determining a second width of the second neural measurement, and calculating a difference between the first width and second width.

5. The method of claim 1, wherein the neural response decay is determined as being a ratio of an amplitude or strength of the first neural measurement to an amplitude or strength of the second neural measurement.

6. The method of claim 3, further comprising dividing the difference by an amplitude normalizing term comprising a sum of scalar variants of the first amplitude and second amplitude.

7. The method of claim 3, wherein the first amplitude is determined at a first moment of the first measurement corresponding to an expected occurrence of the neural response, the first moment being determined by reference to a timing of the electrical stimulus and a distance from a stimulus site to the first sense electrode, and wherein the second amplitude is determined at a second moment of the second measurement corresponding to an expected occurrence of the neural response, the second moment being determined by reference to the timing of the electrical stimulus and a distance from the stimulus site to the second sense electrode.

8. The method of claim 5, wherein the method is repeated in order to obtain a plurality of ratios resulting from repeated application of a given stimulus in order to give a probabilistic indication of the neural response decay to improve the determination of whether a locally evoked response is present.

9. The method of claim 5, wherein the method is performed repeatedly in order to monitor changes in the ratio which occur over time.

10. The method of claim 1, further comprising the step of using a signal quality indicator to detect whether any neural activity is present to avoid false positives.

11. The method of claim 1, further comprising obtaining a contemporaneous third or additional neural measurement from a third or additional sense electrode(s) spaced apart from the first and second electrodes along the neural pathway.

12. A method for detecting locally evoked neural responses in neural measurements obtained in the presence of distally evoked neural responses, the method comprising:

applying, by an implantable device, an electrical stimulus to a neural pathway;

obtaining, by the implantable device, a first neural measurement from a first sense electrode coupled to the implantable device;

obtaining, by the implantable device, a contemporaneous second neural measurement from a second sense electrode coupled to the implantable device and spaced apart from the first electrode along the neural pathway;

determining, by the implantable device, a neural response decay, the neural response decay being a measure of decay in a neural response from the first sense electrode to the second sense electrode, from the first neural measurement and the second neural measurement; and determining, by the implantable device, from the neural response decay whether a locally evoked neural response is present in the neural measurements by distinguishing the locally evoked neural response from distally evoked neural responses; and applying, by the implantable device, neurostimulation in response to the determining from the neural response decay whether a locally evoked neural response is present in the neural measurements.

13. The method of claim 12, wherein distinguishing the locally evoked response from the distally evoked responses comprises determining from the neural response decay that the locally evoked neural response is synchronized to the stimulus, or that the distally evoked neural response is not synchronized to the stimulus.

14. An implantable device for detecting locally evoked neural responses in neural measurements obtained in the presence of distally evoked neural responses, the device comprising:

a stimulus source for applying an electrical stimulus to a neural pathway;

measurement circuitry for obtaining a first neural measurement from a first sense electrode, and for obtaining a contemporaneous second neural measurement from a second sense electrode spaced apart from the first electrode along the neural pathway; and a processor configured to:
determine from the first neural measurement and the second neural measurement a neural response decay, the neural response decay being a measure of decay in a neural response from the first sense electrode to the second sense electrode;
determine from the neural response decay whether a locally evoked neural response is present in the neural measurement; and
apply neurostimulation in response to the determining from the neural response decay whether a locally evoked neural response is present in the neural measurements.

15. A non-transitory computer readable medium for detecting locally evoked neural responses in neural measurements obtained in the presence of distally evoked neural responses, comprising instructions which, when executed by one or more processors, causes performance of the following:

applying, by an implantable device, an electrical stimulus to a neural pathway;

obtaining, by the implantable device, a first neural measurement from a first sense electrode coupled to the implantable device;

obtaining, by the implantable device, a contemporaneous second neural measurement from a second sense electrode coupled to the implantable device and spaced apart from the first electrode along the neural pathway;

determining, by the implantable device, a neural response decay, the neural response decay being a measure of decay in a neural response from the first sense electrode to the second sense electrode, from the first neural measurement and the second neural measurement;

determining, by the implantable device, from the neural response decay whether a locally evoked neural response is present in the neural measurements; and applying, by the implantable device, neurostimulation in response to the determining from the neural response decay whether a locally evoked neural response is present in the neural measurements.

16. The implantable device of claim 14, wherein the processor is configured to determine the neural response decay by determining a first amplitude of the first neural measurement, determining a second amplitude of the second neural measurement, and calculating a difference between the first amplitude and the second amplitude.

17. The implantable device of claim 16, wherein the processor is configured to divide the difference by an amplitude normalizing term comprising a sum of scalar variants of the first amplitude and second amplitude.

18. The implantable device of claim 14, wherein the processor is configured to determine the neural response decay by determining a first width of the first neural measurement, determining a second width of the second neural measurement, and calculating a difference between the first width and second width.

19. The implantable device of claim 14, wherein the processor is configured to determine the neural response decay as being a ratio of an amplitude or strength of the first neural measurement to an amplitude or strength of the second neural measurement.

20. The implantable device of claim 14, wherein the processor is configured to determine the first amplitude at a first moment of the first measurement corresponding to an expected occurrence of the neural response, the first moment being determined by reference to a timing of the electrical stimulus and a distance from a stimulus site to the first sense electrode, and wherein the processor is configured to determine the second amplitude at a second moment of the second measurement corresponding to an expected occurrence of the neural response, the second moment being determined by reference to the timing of the electrical stimulus and a distance from the stimulus site to the second sense electrode.

21. The implantable device of claim 19, wherein the processor is configured to repeatedly detect whether a locally evoked neural response is present in the neural measurement, in order to obtain a plurality of ratios resulting from repeated application of a given stimulus in order to give a probabilistic indication of the neural response decay to improve the determination of whether a locally evoked response is present.

22. The implantable device of claim 14, further comprising a signal quality indicator to detect whether any neural activity is present to avoid false positives.

23. The implantable device of claim 14, wherein the processor is configured to use the determined presence of the locally evoked neural response to characterize the performance of a local electrical stimulus regime.

* * * * *